United States Patent [19]
Gubler et al.

[11] Patent Number: 5,852,176
[45] Date of Patent: Dec. 22, 1998

[54] ANTIBODIES TO RECEPTORS FOR HUMAN INTERLEUKIN-12

[75] Inventors: Ulrich Andreas Gubler; David Howard Presky, both of Glen Ridge, N.J.

[73] Assignee: Hoffmann-La Roche Inc., Nutley, N.J.

[21] Appl. No.: 915,495

[22] Filed: Aug. 20, 1997

Related U.S. Application Data

[62] Division of Ser. No. 685,118, Jul. 23, 1996.

[60] Provisional application Nos. 60/001,701 Aug. 1, 1995, and 60/018,674, May 30, 1996.

[51] Int. Cl.⁶ .................................................. C07K 16/28
[52] U.S. Cl. .............................. 530/389.2; 530/388.22; 424/143.1; 435/70.21
[58] Field of Search ........................... 530/388.22, 389.2; 424/143.1

[56] References Cited

U.S. PATENT DOCUMENTS 5,536,657   7/1996   Chua et al. ............................. 435/69.1

FOREIGN PATENT DOCUMENTS 0 638 644   2/1995   European Pat. Off. .

OTHER PUBLICATIONS

Chizzonite et al. *Cytokine* 6(5) 1994, p. A82a.
Presky et al, *Res Immunol* 146, 1995, pp. 439–445.
Chizzonite et al, *J. Immunol.* 147(5) 1991, pp. 1548–1556.
Meajer et al, *Lancet* 350, 1997, pp. 1596–1597.
Marth et al, *Gastroenterology* 110(4) 1996, p. A958.
Gately, M.K. et al., 1991, J. Immunol. 147:874.
Kobayashi, M., et al., 1989, J. Exp. Med. 170:827.
Stern, A.S. et al., 1990, Proc. Natl. Acad. Sci. USA 87:6808.
Gately, M.K., 1992, Cell Immunology 143:127.
Chan, S.H. et al., 1991, J. Exp. Med. 173:869.
Manetti, R., et al., 1993, J. Exp. Med. 177:1199.
Hsieh, C.S. et al., 1993, Science 260:547.
Chizzonite, R., et al., 1992, J. Immunol. 148:3117.
Desai, B., et al., J. Immunol, 1992, 148:3125.
Desai, B., et al., 1993, J. Immunol. 150:207A.
Chizzonite, R., et al., 1994, Cytokine 6(5):A82a.
Chua, A., et al., 1994, J. Immunology 153:128.
Stahl & Yancopoulos, 1993, Cell 74:587.
Charnow, S.M., et al., Trends in Biotechnology vol. 14 52–60 (1996).
M.O. Dayhoff, et al., Methods Enzymology 91:524 (1983).
U. Gubler, et al., 1991, Proc. Natl. Acad. Sci USA 88:4143.
H.W. Lahm et al. 1985, J. Chromatog. 326:357.
S. Mizushima & S. Nagata, Nucl. Acids Res. 1990 18:5322.
S. Grant. et al. 1990, Proc. Natl. Acad. Sci. USA 87:4645.
Gately, et al., J. Natl. Cancer Inst. 69 1245 (1982).
P. Chomczynski & N. Sacchi, Anal. Biochem. 162: 156, 1987.
K. Kuribayashi et al. Nucl. Acids Res. Symposium Series 19:61, 1988.
U. Gubler & A. Chua, Essential Molecular Biology vol. II, T.A. Brown, editor pp. 39–56 TRL Press 1991.
A. Aruffo & B. Seed, Proc. Natl. Acad. Sci (USA) 94, 8573, 1987.
Hara & Miyajima 1992, EMBO 11:1875.
Grunstein & Hogness, Molecular Cloning Proc. Nat. Acad. Sci. USA 72:3961 (1975).
McPherson J., 1985, Pharmacol Methods, 14:213.
Palacios R., et al., 1985, Cell 41:727.
Giordano, T. J. et al., 1990, Gene 88:285.
vonHeijne G., 1986, Nucl. Acids Research 14;4683.
Presky, D., et al., Res. Immunol. 146 439–445 (1995).
Ellison et al., Nucl. Acid Res. 10 4071–4079.
Huck, et al., Nucl. Acid Res 14 1779–1789 (1986).
Presky, et al., PNAS 93(24), pp. 14002–14007 (1996).
Gubler, et al., FASEB J. 10(6), A1326 (1996).
Szabo et al., FASEB J. 10(6), A1310 (1996).

*Primary Examiner*—Garnette D. Draper
*Attorney, Agent, or Firm*—George W. Johnston; Patricia S. Rocha-Tramaloni; Robert A. Silverman

[57] ABSTRACT

Antibodies to human IL-12 beta 2 receptor protein or an IL-12 receptor complex, the complex comprising the beta1 receptor protein complexed with a beta2 receptor protein, which complex is capable of binding to human IL-12 with high affinity.

1 Claim, No Drawings

ANTIBODIES TO RECEPTORS FOR HUMAN INTERLEUKIN-12

This is a division of application Ser. No. 08/685,118 filed Jul. 23, 1996, which claims priority from Provisional applications 60/001,701 and 60/018,674 filed Aug. 1, 1995 and May 30, 1996, respectively.

FIELD OF INVENTION

This invention relates generally to human Interleukin-12 receptors.

BACKGROUND OF THE INVENTION

Interleukin-12 (IL-12), formerly known as cytotoxic lymphocyte maturation factor or natural killer cell stimulatory factor, is a 75-KDa heterodimeric cytokine composed of disulfide-bonded 40-KDa (p40) and 35-KDa (p35) subunits that has multiple biological activities including stimulation of the proliferation of activated T and NK cells (Gately, M. K., et al., 1991, J. Immunol., 147:874) (Kobayashi, M., et al., 1989, J. Exp. Med., 170:827), enhancement of the lytic activity of NK/LAK cells (Kobayashi, M., et al., 1989, J. Exp. Med., 170:827; Stern, A. S., et al., 1990, Proc. Natl. Acad. Sci. USA, 87:6808), enhancement of cytolytic T-cell responses (Gately, M. K., et al., 1992, Cell. Immunology, 143:127), induction of interferon gamma by resting and activated T- and NK-cells (Kobayashi, M. et al., 1989, J. Exp. Med., 170:827; Chan, S. H., et al., 1991, J. Exp. Med., 173:869), and promotion of $T_h1$-type helper cell responses (Manetti, R., et al., 1993, J. Exp. Med., 177:1199; Hsieh, C. -S., et al., 1993, Science 260:547).

The biological activity of IL-12 is mediated by the binding of the IL-12 molecules to cell surface, or plasma membrane, receptors on activated T- and NK cells; however, the contributions of the individual subunits, p35 and p40, to receptor binding and signal transduction remain unknown. Studies with labeled IL-12 have shown that this binding occurs in a specific and saturable manner. IL-12 delivers a signal to target cells through a receptor that was initially characterized on phytohaemagglutinin (PHA)-activated CD4+ and CD8+ T-cells and on IL-2 activated CD56+ NK-cells (Chizzonite, R., et al., 1992, J. Immunol., 148:3117; Desai, B., et al., 1992, J. Immunol., 148:3125).

A survey of over 20 human cell lines belonging to the T-, B-, NK- and myelomonocytic lineages only identified a single CD4+, IL-2 dependent human T-cell line (Kit 225/K6) that constitutively expresses the IL- 12 receptor and responds to IL-12 (Desai, B., et al., 1992, J. Immunol., 148:3125; Desai, B., et al., 1993, J. Immunol. 150:207A). Freshly prepared PHA-activated peripheral blood mononuclear cells (PBMC) and the Kit 225/K6 cell line thus represent two convenient cell sources to study the biochemistry of the functional IL-12 receptor; there may be others.

Equilibrium binding experiments with $^{125}$I-labeled IL-12 identified three sites with binding affinities for human IL-12 of 5–20 pM, 50–200 pM, and 2–6 nM on IL-12 responsive T-cells (Chizzonite, R., et al., 1994, Cytokine 6(5):A82a).

A cDNA encoding a low affinity IL-12 receptor was previously cloned (Chua, A., et al, 1994, J. Immunology 153:128; U.S. patent application Ser. No. 08/248,532, filed May 31, 1994 (incorporated herein by reference)). Based on a previously suggested nomenclature (Stahl and Yancopoulos, 1993, Cell 74:587), we now call the initially isolated human IL-12 receptor chain the beta1 chain. However, because (i) this isolated human IL-12 beta1 receptor chain binds human IL-12 with low affinity, and (ii) IL-12 responsive T-cells have a high affinity binding site for human IL-12, another human IL-12 receptor chain must exist.

SUMMARY OF THE INVENTION

We have found that the IL-12 receptor comprises a complex of the beta1 receptor protein with a beta2 receptor protein, which complex is capable of binding to human IL-12 with high affinity. We have isolated the DNA encoding the human IL-12 beta2 receptor protein and produced a recombinant human IL-12 beta2 receptor protein on the surface of a non-human mammalian cell, free from other human proteins, in its active form. In addition, we produced a recombinant human IL-12 receptor complex on the surface of a non-human mammalian cell, free from other human proteins, having a high binding affinity for human IL-12. In addition, we produced a non-human mammalian cell having expressed on its surface the recombinant human IL-12 beta2 receptor protein, which cell proliferates in the presence of human IL-12. In addition, we produced a non-human mammalian cell having expressed on its surface the recombinant human IL-12 receptor complex, which cell proliferates in the presence of human IL-12.

In accordance with this invention, a non-human mammalian cell having the human IL-12 beta2 receptor protein or the complex expressed on its surface and which proliferates in response to human IL-12 is useful for determining IL-12 bioactivity. For example, such cells are useful for determining whether a given compound inhibits biological activity of human IL-12 or is an IL-12 agonist.

In addition, through the ability to express the human IL-12 beta2 receptor protein on a non-human mammalian cell surface, we can also express fragments of the human IL-12 beta2 receptor protein, and can determine whether these fragments, when complexed with the beta1 subunit, or an active fragment thereof, have the same properties and high binding affinity for IL-12 as the intact complex.

We can use the isolated DNA encoding the human IL-1 2 beta2 receptor protein to make a purified, recombinant protein which is soluble, and which binds to IL-12 with the same affinity as human IL-12 beta2 receptor protein. We can also use the isolated DNA encoding the human IL-12 beta2 receptor protein to make a purified, recombinant protein which is soluble, and which binds to IL-12 with the same affinity as the recombinant human IL-12 receptor complex of the beta1 receptor protein with the beta2 receptor protein [See, for example, Charnow, S. M. et al., Trends in Biotechnology, Vol. 14, 52–60 (1996)].

Such purified, recombinant proteins, which bind to human IL-12, are useful for preventing or treating pathological conditions caused by excess or inappropriate activity of cells possessing IL-12 receptors, by inhibiting binding of IL-12 to such cells. Pathological conditions caused by excess activity of cells possessing IL-12 receptors include autoimmune dysfunctions, such as without limitation rheumatoid arthritis, inflammatory bowel disease, and multiple sclerosis.

A purified, recombinant protein which is soluble, and which binds to IL-12 with the same affinity as human IL-12 beta2 receptor protein is the fusion of a soluble fragment of human IL-12 beta2 receptor protein and a human Ig heavy chain (such as IgG, IgM or IgE, preferably IgG) having all domains except the first domain of the constant region. This recombinant protein is encoded by a chimeric polynucleotide which has 2 DNA subsequences fused in frame. The first DNA subsequence, at the 5' end of the chimeric polynucleotide, is an isolated DNA sequence encoding a soluble fragment of human IL-12 beta2 receptor protein. The second DNA subsequence, located at the 3' end of the chimeric polynucleotide, is an isolated DNA sequence encoding all domains of a human heavy chain Ig (preferably IgG) except the first domain of the constant region. The desired recombinant protein can be generated by transfection of the chimeric polynucleotide into a non-human mammalian cell, such as a chinese hamster ovary (CHO) cell. The expressed recombinant protein can be purified, for example, by protein G affinity chromatography.

A purified, recombinant protein which is soluble, and which binds to IL-12 with the same affinity as the recombinant human IL-12 receptor complex of the beta1 receptor with the beta2 receptor is encoded by two chimeric polynucleotides which each have two DNA subsequences fused in frame. The first DNA subsequence of the first chimeric polynucleotide, located at the 5' end, is an isolated DNA sequence encoding a soluble fragment of human IL-12 beta2 receptor protein. The second DNA subsequence of the first chimeric polynucleotide, located at the 3' end, is an isolated DNA sequence encoding all domains of a human Ig heavy chain (for example, IgG, IgM, IgE, preferably IgG) except the first domain of the constant region. The first DNA subsequence of the second chimeric polynucleotide, located at the 5' end, is an isolated DNA sequence encoding a soluble fragment of human IL-12 beta1 receptor protein. The second DNA subsequence of the second chimeric polynucleotide, located at the 3' end, is an isolated DNA sequence encoding all domains of a human Ig heavy chain (for example, IgG, IgM, IgE, preferably IgG) except the first domain of the constant region. The desired recombinant protein may be generated by cotransfection of the two chimeric polynucleotides into a non human mammalian cell, such as a CHO cell. The expressed protein can be purified, for example, by any method that enables differentiation of homodimeric proteins from heterodimeric proteins, such as, for example, column chromatography.

In addition, monoclonal or polyclonal antibodies directed against the human IL-12 beta2 receptor protein, or fragments thereof, or the complex, may also be produced by known methods [See, for example, Current Protocols in Immunology, edt. by Coligan, J. E. et al., J. Wiley & Sons (1992)] and used to prevent or treat pathological conditions caused by excess activity of cells possessing IL-12 receptors by inhibiting binding of IL-12 to such cells.

DETAILED DESCRIPTION OF THE INVENTION

We have found that the human IL-12 receptor comprises a complex of the beta1 receptor protein with the beta2 receptor protein, which complex is capable of binding to human IL-12 with high affinity. We have isolated the DNA encoding the human IL-12 beta2 receptor protein and produced a recombinant human IL-12 beta2 receptor protein on the surface of a non-human mammalian cell, free from other human proteins, in its active form. In addition, we produced a recombinant human IL-12 receptor complex on the surface of a non-human mammalian cell, free from other human proteins, having a high binding affinity for human IL-12. In addition, we produced a non-human mammalian cell having expressed on its surface the recombinant human IL-12 beta2 receptor protein, which cell proliferates in the presence of human IL-12. In addition, we produced a non-human mammalian cell having expressed on its surface the recombinant human IL-12 receptor complex, which cell proliferates in the presence of human IL-12.

The following terms shall have the following definitions set forth below:

Human IL-12 beta2 receptor protein refers to (1) the protein of SEQ ID NO:2, or (2) any protein or polypeptide having an amino acid sequence which is substantially homologous to the amino acid sequence SEQ ID NO:2 and which has the following properties:

1) The protein or polypeptide has low binding affinity for human IL-12, and
2) The protein or polypeptide, when complexed with human beta1 receptor protein forms a complex having high binding affinity for human IL-12.

Human IL-12 beta1 receptor protein refers to (1) the protein of SEQ ID NO:4, or (2) any protein or polypeptide having an amino acid sequence which is substantially homologous to the amino acid sequence SEQ ID NO:4 and which has the following properties:

1) The protein or polypeptide binds to has low binding affinity for human IL-12, and
2) The protein or polypeptide, when complexed with human beta2 receptor protein forms a complex having high binding affinity for human IL-12.

As used herein, the terms human IL-12 beta2 receptor protein and human IL-12 beta1 receptor protein includes proteins modified deliberately, as for example, by site directed mutagenesis or accidentally through mutations.

Substantially homologous, which can refer both to nucleic acid and amino acid sequences, means that a particular subject sequence, for example, a mutant sequence, varies from the reference sequence by one or more substitutions, deletions, or additions, the net effect of which do not result in an adverse functional dissimilarity between the reference and subject sequences. For purposes of the present invention, sequences having greater than 95% homology, equivalent biological properties, and equivalent expression characteristics are considered substantially homologous. For purposes of determining homology, truncation of the mature sequence should be disregarded. Sequences having lesser degrees of homology, comparable bioactivity, and equivalent expression characterisitics are considered substantial equivalents. Generally, homologous DNA sequences can be identified by cross-hybridization under high stringency hybridization conditions.

Fragment of the human IL-12 beta2 receptor protein means any protein or polypeptide having the amino acid sequence of a portion or fragment of human IL-12 beta2 receptor protein, and which (a) has low binding affinity for human IL-12, and (2) when complexed with a human IL-12 beta1 receptor protein, forms a complex having high binding affinity for human IL-12.

Fragment of the human IL-12 beta1 receptor protein means any protein or polypeptide having the amino acid sequence of a portion or fragment of human IL-12 beta1 receptor protein, and which when complexed with a human IL-12 beta2 receptor protein, forms a complex having high binding affinity for human IL-12.

Expression vector is a genetic element capable of replication under its own control, such as a plasmid, phage or cosmid, to which another DNA segment may be attached so as to bring about the replication of the attached segment. It comprises a transcriptional unit comprising an assembly of (1) a genetic element or elements having a regulatory role in gene expression, for example, promoters and enhancers, (2) a structural or coding sequence which is transcribed into mRNA and translated into protein, and (3) appropriate transcription initiation and termination sequences.

Clone is a group of identical DNA molecules derived from one original length of DNA sequence and produced by a bacterium or virus using genetic engineering techniques, often involving plasmids.

Soluble fragment refers to a fragment of a human IL-12 receptor protein having an amino acid sequence corresponding to all or part of the extracellular region of the protein and which retains the IL-12 binding activity of the intact IL-12 receptor protein. For example, a soluble fragment of a human IL-12 beta2 receptor protein is a fragment of a human IL-12 beta2 receptor protein having an amino acid sequence corresponding to all or part of the extracellular region of a human IL-12 beta2 receptor protein.

Expression of human IL-12 receptor protein having high binding affinity to human IL-12

The cDNA of cells where the human IL-12 receptor is known to be found is incorporated by conventional methods into a bacterial host to establish a cDNA library. PHA-activated PBMC and cells from the Kit 225/K6 cell line are examples of cell sources for the cDNA. RNA from the cells is extracted, characterized, and transcribed into single stranded cDNA by conventional methods. The single stranded cDNA is converted into double stranded cDNA by conventional methods. The double stranded cDNA is incorporated by conventional techniques into an expression vector, such as pEF-BOS. The plasmid DNA from the expression vector is then incorporated into a bacterial host by conventional methods to form a library of recombinants.

The cDNA library is screened by conventional expression screening methods, as described by Hara and Mijayima, 1992. EMBO, 11:1875, for cDNA's which when expressed with cDNA's for the human IL-12 beta1 receptor protein, give rise to a high affinity human IL-12 receptor. A small number of clones from the library are grown in pools. DNA is extracted by conventional methods from the pools of clones. The DNA extracted from a pool of clones is then transfected by conventional methods, along with a small amount of DNA from a plasmid containing the cDNA encoding the human IL-12 beta1 receptor protein, into non-human host cells. The non-human host cells are preferably mammalian, such as a COS cell. Labeled recombinant human IL-12 is then added to the non-human host cells previously transfected as described above and the binding signal of the pool is determined. This process is repeated for each pool. The pools showing a positive binding signal for IL-12 may then be subsequently broken down into smaller pools and reassayed in the above manner until a single clone is selected which shows a positive binding signal.

The plasmid DNA from the selected clone is sequenced on both strands using conventional methods, such as an ABI automated DNA sequencer in conjunction with a thermostable DNA polymerase and dye-labeled dideoxynucleotides as terminators. Amino acid sequence alignments may be run as described by M. O. Dayhoff et al., Methods Enzymology 91:524 (1983) with the mutation data matrix, a break penalty of 6 and 100 random runs.

The DNA from the selected clone is then co-transfected by conventional methods with DNA from a plasmid containing the cDNA encoding the human IL-12 beta1 receptor protein into a non-human host cell, preferably a non-human mammalian cell such as a COS cell or a Ba/F3 cell.

Alternatively, by conventional recombinant methods, a plasmid may be engineered which contains transcription units (promoter, cDNA, and polyA regions) for both human IL-12 beta1 receptor protein and human IL-12 beta2 receptor protein. Plasmid DNA is transfected by conventional methods into a non-human host cell, preferably a non-human mammalian cell such as a COS cell or a Ba/F3 cell.

In accordance with the invention, a complex comprising human IL-12 beta2 receptor protein, or a fragment thereof, complexed with human IL-12 beta1 receptor protein, or a fragment thereof, may be expressed on the cell surface of the non-human host cell. When expressed on the cell surface of the non-human host cell, the complex has a high binding affinity for human IL-12, whereas the human IL-12 beta 1 receptor protein and the human IL-12 beta2 receptor protein alone each have a low binding affinity for human IL-12.

In accordance with this invention, we can also express on the surface of a non-human host cell human IL-12 beta2 receptor protein.

In accordance with this invention, not only can the human IL-12 beta2 receptor protein be obtained, we can also obtain fragments of human IL-12 beta2 receptor protein which (1) has low binding affinity for human IL-12 and (2) which when complexed with a human IL-12 beta1 receptor protein forms a complex having high binding affinity. The fragments of human IL-12 beta2 receptor protein may be obtained by conventional means, such as (i) proteolytic degradation of the human IL-12 beta2 receptor protein, (ii) chemical synthesis by methods routine in the art, or (iii) standard recombinant methods.

For purposes of the present invention, a human IL-12 receptor protein which has a high binding affinity for human IL-12 is a protein which binds to human IL-12 with a binding affinity of from about 5 to about 100 pM. For purposes of the present invention, a human IL-12 receptor protein which has a low binding affinity for human IL-12 is a protein which binds to human IL-12 with a binding affinity of from about 1 to about 10 nM. The binding affinity of a protein for human IL-12 can be determined by conventional means, such as desribed in R. Chizzonite et al., 1992, J. Immunol., 148:3117 and as set forth in Example 5.

Fragments of human IL-12 beta2 receptor protein can also be measured for binding affinity for human IL-12 by conventional means, such as desribed in R. Chizzonite et al., 1992, J. Immunol., 148:3117 and as set forth in Example 5. The fragments of human IL-12 beta2 receptor protein may be measured for binding affinity for human IL-12 either alone or complexed with human IL-12 beta1 receptor protein, or a fragment of human IL-12 beta1 receptor protein which when complexed with a human IL-12 beta2 receptor protein forms a complex having high binding affinity.

In accordance with this invention, we can isolate DNA which encodes a complex capable of binding to human IL-12 with high affinity, the complex comprising human IL-12 beta2 receptor protein, or a fragment thereof, and human IL-12 beta1 receptor protein, or a fragment thereof.

In accordance with this invention, we can also isolate DNA which encodes human IL-12 beta2 receptor protein, or a fragment thereof, which fragment (1) has low binding affinity for human IL-12 and (2) when complexed with human IL-12 beta1 receptor protein, forms a complex having high binding affinity for human IL-12.

An isolated DNA sequence refers to a DNA polymer, in the form of a separate fragment or as a component of a larger DNA construct, which has been derived from DNA isolated at least once in substantially pure form, that is, free of contaminating endogenous materials and in a quantity or concentration enabling identification, manipulation, and recovery of the sequence and its component nucleotide sequences by standard biochemical methods, for example, using a cloning vector. Such sequences are preferably provided in the form of an open reading frame uninterrupted by internal nontranslated sequences, or introns, which are typically present in eukaryotic genes. Genomic DNA containing the relevant sequences could also be used as a source of coding sequences. Sequences of non-translated DNA may be present 5' or 3' from the open reading frame, where the same do not interfere with manipulation or expression of the coding regions.

In accordance with this invention, we can also make, by known methods, a purified, recombinant protein which is the fusion of a soluble fragment of human IL-12 beta2 receptor protein and a human Ig heavy chain (preferably IgG) containing all domains except the first domain of the constant region. This recombinant protein, which is homodimeric, is encoded by a chimeric polynucleotide which has 2 DNA subsequences fused in frame. The first DNA subsequence, at the 5' end of the chimeric polynucleotide, is an isolated DNA sequence encoding a soluble fragment of human IL-12 beta2 receptor protein. The second DNA subsequence, located at the 3' end of the chimeric polynucleotide, is an isolated DNA sequence encoding all domains of a human Ig heavy chain (preferably IgG) except the first domain of the constant region.

In addition, we can make, by known methods, a purified, recombinant protein comprising two different polypeptide chains (a heterodimeric protein). The two different polypeptide chains are each encoded by a different chimeric polynucleotide which has two DNA subsequences fused in frame. The first DNA subsequence of the first chimeric polynucleotide, located at its 5' end, is an isolated DNA sequence encoding a soluble fragment of human IL-12 beta2 receptor protein. The second DNA subsequence of the first chimeric polynucleotide, located at its 3' end, is an isolated DNA sequence encoding all domains of a human Ig heavy chain (preferably IgG) except the first domain of the constant region. The first DNA subsequence of the second chimeric polynucleotide, located at its 5' end, is an isolated DNA sequence encoding a soluble fragment of human IL-12 beta1 receptor protein. The second DNA subsequence of the second chimeric polynucleotide, located at its 3' end, is an isolated DNA sequence encoding all domains of a human Ig heavy chain (preferably IgG) except the first domain of the constant region.

The starting materials for the purified, recombinant proteins of the invention may be obtained by methods known in the art. In particular, on the basis of the DNA sequence coding for human IL-12 beta2 receptor protein described in SEQ ID NO: 1 and of the already known DNA sequences for certain receptors, those partial DNA sequences which code for a soluble fragment of human IL-12 beta2 receptor protein can be determined and engineered from the DNA sequence coding for human IL-12 beta2 receptor protein described in SEQ ID NO: 1 using known methods, see Sambrook et al., "Molecular Cloning", 2nd ed., Cold Spring Harbor Laboratory Press (1989). Similarly, on the basis of the DNA sequence coding for human IL-12 beta1 receptor protein described in SEQ ID NO: 3 and of the already known DNA sequences for certain receptors, those partial DNA sequences which code for a soluble fragment of human IL-12 beta1 receptor protein can be determined and engineered from the DNA sequence coding for human IL-12 beta1 receptor protein described in SEQ ID NO: 3 using known methods, see Sambrook et al., "Molecular Cloning", 2nd ed., Cold Spring Harbor Laboratory Press (1989). Sources for isolated DNA sequences coding for constant domains of human immunoglobulins are known in the art and disclosed, for example, by Ellison et al., Nucl. Acid Res. 10, 4071–4079 (1982) for IgG, or Huck et al., Nucl. Acid Res. 14, 1779–1789 (1986) for $IgG_3$.

The isolated DNA sequence encoding the soluble fragment of human IL-12 beta2 receptor protein may be fused in frame, by known methods [Sambrook et al., "Molecular Cloning", 2nd ed., Cold Spring Harbor Laboratory Press (1989)], to the isolated DNA sequence encoding all domains of a human Ig heavy chain (preferably IgG) except the first domain of the constant region. The resulting chimeric polynucleotide has located at its 5' end the isolated DNA sequence encoding the soluble fragment of human IL-12 beta2 receptor protein and at its 3' end the isolated DNA sequence encoding all domains of the human Ig heavy chain except the first domain of the constant region.

Similarly, the isolated DNA sequence encoding the soluble fragment of human IL-12 beta1 receptor protein may be fused in frame, by known methods [Sambrook et al., "Molecular Cloning", 2nd ed., Cold Spring Harbor Laboratory Press (1989)], to the isolated DNA sequence encoding all domains of a human Ig heavy chain (preferably IgG) except the first domain of the constant region. The resulting chimeric polynucleotide has located at its 5' end the isolated DNA sequence encoding the soluble fragment of human IL-12 beta1 receptor protein and at its 3' end the isolated DNA sequence encoding all domains of a human Ig heavy chain except the first domain of the constant region.

The chimeric polynucleotides can then be integrated using known methods [Sambrook et al., "Molecular Cloning", 2nd ed., Cold Spring Harbor Laboratory Press (1989)] into suitable expression vectors for expression in a non-human mammalian cell, such as a CHO cell. In order to make the homodimeric protein of the invention, the chimeric polynucleotide having located at its 5' end the isolated DNA sequence encoding the soluble fragment of human IL-12 beta2 receptor protein is integrated into a suitable expression vector. In order to make the heterodimeric protein of the invention, the chimeric polynucleotide having located at its 5' end the isolated DNA sequence encoding the soluble fragment of human IL-12 beta2 receptor protein and the chimeric polynucleotide having located at its 5' end the isolated DNA sequence encoding the soluble fragment of human IL-12 beta1 receptor protein are integrated into a single suitable expression vector, or two separate suitable expression vectors.

Preferably, the chimeric polynucleotide(s) is/are co-transfected together with a selectable marker, for example neomycin, hygromycin, dihydrofolate reductase (dhfr) or hypoxanthin guanine phosphoribosyl transferase (hgpt) using methods which are known in the art. The DNA sequence stably incorporated in the chromosome can subsequently be amplified. A suitable selection marker for this is, for example, dhfr. Mammalian cells, for example, CHO cells, which contain no intact dhfr gene, are thereby incubated with increasing amounts of methotrexate after transfection has been performed. In this manner, cell lines which contain a higher number of the desired DNA sequence than the unamplified cells can be obtained.

The baculovirus expression system can also be used for the expression of recombinant proteins in insect cells. Post-translational modifications performed by insect cells are very similar to those occurring in mammalian cells. For the production of a recombinant baculovirus which expresses the desired protein a transfer vector is used. A transfer vector is a plasmid which contains the chimeric polynucleotide(s) under the control of a strong promoter, for example, that of the polyhedron gene, surrounded on both sides by viral sequences. The transfer vector is then transfected into the insect cells together with the DNA sequence of the wild type baculovirus. The recombinant viruses which result in the cells by homologous recombination can then be identified and isolated according to known methods. When using the baculovirus expression system, DNA sequences encoding the immunoglobulin part have to be in the form of cDNA.

The expressed recombinant protein may be purified, for example, by known methods. For example, protein G affinity chromatography may be used to purify the homodimeric protein of the invention. Column chromatography, or any other method that enables differentiation between homodimeric proteins and heterodimeric proteins, may be used to purify the heterodimeric protein of the invention.

Such purified, recombinant proteins are useful for preventing or treating pathological conditions caused by excess or inappropriate activity of cells possessing IL-12 receptors by inhibiting binding of IL-12 to such cells.

"Purified", as used to define the purity of a recombinant protein encoded by the combined DNA sequences described above, or protein compositions thereof, means that the protein or protein composition is substantially free of other proteins of natural or endogenous origin and contains less than about 1% by mass of protein contaminants residual of production processes. Such compositions, however, can contain other proteins added as stabilizers, carders, excipients or co-therapeutics. A protein is purified if it is detectable, for example, as a single protein band in a polyacrylamide gel by silver staining.

Purified recombinant proteins as described above (as well as antibodies to the human IL-12 beta2 receptor proteins and fragments thereof, and antibodies to the complex of this invention) can be administered in clinical treatment of autoimmune dysfunctions, such as without limitation rheumatoid arthritis, inflammatory bowel disease and multiple sclerosis.

The purified recombinant proteins described above (as well as antibodies to the human IL-12 beta2 receptor proteins and fragments thereof, and antibodies to the complex of this invention) can be used in combination with other cytokine antagonists such as antibodies to the IL-2 receptor, soluble TNF (tumor necrosis factor) receptor, the IL-1 antagonist, and the like to treat or prevent the above disorders or conditions.

The dose ranges for the administration of the purified, recombinant proteins described above (as well as antibodies to the human IL-12 beta2 receptor proteins and fragments thereof, and antibodies to the complex of this invention) may be determined by those of ordinary skill in the art without undue experimentation. In general, appropriate dosages are those which are large enough to produce the desired effect, for example, blocking the binding of endogenous IL-12 to its natural receptor. The dosage should not be so large as to cause adverse side effects, such as unwanted cross-reactions, anaphylactic reactions, and the like. Generally, the dosage will vary with the age, condition, sex and extent of disease in the patient, counter indications, if any, immune tolerance and other such variables, to be adjusted by the individual physician. The purified, recombinant proteins described above (as well as antibodies to the human IL-12 beta2 receptor proteins and fragments thereof, and antibodies to the complex of this invention) can be administered parenterally by injection or by gradual perfusion over time. They can be administered intravenously, intraperitoneally, intramuscularly, or subcutaneously.

Preparations for parenteral adminstration include sterile aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, alcohol/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replinishers, electrolyte replinishers, such as those based on Ringer's dextrose, and the like. Preservatives and other additives may also be present, such as, for example, anti-micorbials, anti-oxidants, chelating agents, inert gases and the like. See, generally, *Remington's Pharmaceutical Science,* 16th Ed., Mack Eds., 1980.

Assays for determining whether a given compound blocks IL-12 activity

An aspect of the invention is the use of either the human IL-12 beta2 receptor protein or the complex of this invention as a screening agent for pharmaceuticals. In accordance with this invention, we can determine whether a given compound blocks human IL-12 activity or acts as an agonist of IL-12.

A biological activity of human IL-12 is the stimulation of the proliferation of activated T- and NK-cells. Proliferation of activated T-cells causes alloantigen-induced immune responses, such as allograft rejection (such as skin, kidney, and heart transplants) and graft-versus-host reaction in patients who have received bone marrow transplants. This biological activity of human IL-12 is mediated by the binding of the human IL-12 molecules to cell surface receptors on the activated T-cells.

A compound that blocks human IL-12 activity would, therefore, inhibit the proliferation of activated T-cells and would be useful to treat or prevent alloantigen induced immune responses.

In order to determine if a compound blocks human IL-12 activity, first, a plurality of cells having expressed on their surface either the human IL-12 beta2 receptor protein or a fragment thereof, or the complex of the invention, which cells proliferate in the presence of human IL-12, is provided. The human IL-12 beta2 receptor protein or a fragment thereof binds to human IL-12 with low binding affinity, but when complexed with human beta1 receptor protein forms a complex having high binding affinity for human IL-12. The complex of the invention binds to human IL-12 with high binding affinity and comprises a complex of (1) human IL-12 beta2 receptor protein, or a fragment thereof which when complexed with a human IL-12 beta1 receptor protein forms a complex having high binding affinity to human IL-12, and (2) human IL-12 beta1 receptor protein, or a fragment thereof which when complexed with a human IL-12 beta2 receptor protein forms a complex having high binding affinity to human IL-12. Second, the cells are contacted with human IL-12 and the given compound. Third, it is determined whether the presence of the given compound inhibits proliferation of the cells.

In order to determine if a compound is an agonist of human IL-12, first, a plurality of cells having expressed on their surface either the human IL-12 beta2 receptor protein or a fragment thereof, or the complex of the invention, and which cells proliferate in the presence of human IL-12, is provided. The human IL-12 beta2 receptor protein or a fragment thereof binds to human IL-12 with low binding affinity, but when complexed with human beta1 receptor protein forms a complex having high binding affinity for human IL-12. The complex of the invention binds to human IL-12 with high binding affinity and comprises a complex of (1) human IL-12 beta2 receptor protein, or a fragment thereof which when complexed with a human IL-12 beta1 receptor protein forms a complex having high binding affinity to human IL-12, and (2) human IL-12 beta1 receptor protein, or a fragment thereof which when complexed with a human IL-12 beta2 receptor protein forms a complex having high binding affinity to human IL-12. Second, the cells are contacted with human IL-12 or the given compound. Third, it is determined whether the presence of the given compound stimulates proliferation of the cells.

Examples of cells capable of expressing on their surface the complex, which cells proliferate in the presence of human IL-12 include, without limitation, PHA-activated PBMC, Kit 225/K6 cells, and Ba/F3 cells transfected with cDNA for both human IL-12 beta1 receptor protein and human IL-12 beta2 receptor protein. Examples of cells capable of expressing on their surface the human IL-12 beta2 receptor protein, or a fragment thereof, which cells proliferate in the presence of human IL-12 include, without limitation, Ba/F3 cells transfected with cDNA for human IL-12 beta2 receptor protein.

In order to determine whether the presence of the given compound inhibits proliferation of the cells, the following procedure may be carried out. The human IL-12 responsive cells, having expressed on their surface the human IL-12 beta2 receptor protein, or a fragment thereof, or the human IL-12 receptor complex of the invention, are plated into wells of a microtiter plate. Human IL-12 is then added to some wells of the microtiter plate (standard wells) and allowed to react with the cells. The compound to be tested is added either before or simultaneously with human IL-12 to different wells of the microtiter plate (sample wells) and allowed to react with the cells. Any solvent used must be non-toxic to the cell. The proliferation of the cells is then measured by known methods, for example, labeling the cells after contact with human IL-12 and the compound (such as by incorporation of tritiated thymidine into the replicating DNA), measuring the accumulation of cellular metabolites (such as lactic acid), and the like. The proliferation of the cells of the standard wells is compared to proliferation of the cells of the sample wells. If the cells of the sample wells proliferate significantly less than the cells of the standard wells, the compound blocks IL-12 activity.

In order to determine whether the presence of the given compound simulates proliferation of the cells, the following procedure may be carried out. The human IL-12 responsive cells having expressed on their surface the human IL-12 beta2 receptor protein, or a fragment thereof, or the human IL-12 receptor complex of the invention are plated into wells of a microtiter plate. Human IL-12 is then added to some wells of the microtiter plate (standard wells) and allowed to react with the cells. The compound to be tested is added to different wells of the microtiter plate (sample wells) and allowed to react with the cells. Any solvent used must be non-toxic to the cell. The proliferation of the cells is then measured by known methods, for example, labeling the cells after contact with the compound (such as by incorporation of tritiated thymidine into the replicating DNA), measuring the accumulation of cellular metabolites (such as lactic acid), and the like. The proliferation of the cells of the standard wells is compared to proliferation of the cells of the sample wells. If the cells of the sample wells proliferate significantly more than cells that were not exposed to human IL-12, the compound is an agonist of human IL-12.

The following examples are offered by way of illustration, not by limitation.

DETAILED DESCRIPTION OF THE PREFERRED EMBODIMENTS

Materials
Proteins, plasmids and strains
Recombinant human IL-12 (U. Gubler et al., 1991, Proc. Natl. Acad. Sci. USA., 88:4143) was obtained as described therein.

Recombinant human IL-2 (H. W. Lahm et al., 1985, J. Chromatog, 326:357) was obtained as described therein The plasmid pEF-BOS was obtained from Dr. Nagata at the Osaka Bioscience Institute in Japan. The plasmid is based on a pUC 119 backbone and contains the elongation factor 1 alpha promoter to drive expression of genes inserted at the BstXI site (S. Mizushima and S. Nagata, Nucl. Acids Res., 1990, 18:5322).

The human IL-12 receptor beta1 cDNA in the plasmid pEF-BOS was obtained as described in A. Chua et al., 1994, J. Immunology 153:128 and in U.S. patent application Ser. No. 08/248,532, filed May 31, 1994.

Electrocompetent E. coli DH-10B (S. Grant et al., 1990, Proc. Natl. Acad. Sci USA 87:4645) was obtained from Bethesda Research Laboratory (Bethesda, Md.).

Methods
Labeling of human IL-12 with $^{125}I$

Recombinant human IL-12 was labeled with $^{125}I$ as follows. Iodogen was dissolved in chloroform. 0.05 mg aliquots of Iodogen were dried in 12×150 mm borosilicate glass tubes. For radiolabeling, 1.0 mCi Na[$^{125}I$] was added to the Iodogen-coated borosilicate glass tube, which also contained 0.05 ml of Tris-iodination buffer (25 mM Tris-HCL pH 7.5, 0.4M NaCl and 1 mM EDTA) to form a $^{125}I$ solution. The 125I solution was activated by incubating for 6 minutes at room temperature. The activated $^{125}I$ solution was transferred to a tube containing 0.05 to 0.1 ml recombinant human IL-12 (31.5 μg) in Tris-iodination buffer. The resulting mixture of the activated $^{125}I$ solution and the recombinant human IL-12 was incubated for 6 minutes at room temperature. At the end of the incubation, 0.05 ml of Iodogen stop buffer (10 mg/ml tyrosine, 10% glycerol in Dulbecco's phosphate buffered saline (PBS), pH 7.40) was added and reacted for 3 minutes. The resulting mixture was then diluted with 1.0 ml Tris-iodination buffer containing 0.25% bovine serum albumin (BSA), and applied to a Bio-Gel P10DG desalting column for chromatography. The column was eluted with Tris-iodination buffer containing 0.25% BSA. 1 ml fractions containing the eluted peak amounts of labeled recombinant human IL-12 were combined. The combined fractions were diluted to 1×10$^8$ cpm/ml with 1% BSA in Tris-iodination buffer. Incorporation of $^{125}I$ into recombinant human IL-12 was monitered by precipitation with trichloroacetic acid (TCA). The TCA precipitable radioactivity (10% TCA final concentration) was typically in excess of 95% of the total radioactivity. The radiospecific activity of the labeled recombinant human IL-12 was typically 1000 to 2000 cpm/fmole.

EXAMPLE 1
Preparation of Human PHA-activated Lymphoblasts

Human peripheral blood mononuclear cells (PBMC) were isolated from blood collected from healthy donors as described in Gately et al., J. Natl. Cancer Inst. 69, 1245 (1982). The blood was collected into heparinized syringes, diluted with an equal volume of Hank's balanced salt solution and layered over lymphocyte separation medium (LSM® obtained from Organon Teknika Corporation, Durham, N.C.) in tubes. The tubes were spun at 2000 rpm for 20 minutes at room temperature. PBMC at the interface of the aqueous blood solution and the lymphocyte separation medium were collected. Collected PBMC were pelleted at 1500 rpm for 10 minutes through a 15 ml cushion of 20% sucrose in Hank's balanced salt solution. Pelleted PBMC were resuspended in tissue culture medium (1:1 mixture of RPMI 1640 and Dulbecco's modified Eagle's medium, supplemented with 0.1 mM nonessential amino acids, 60 μg/ml arginine HCl, 10 mM Hepes buffer, 2 μM L-glutamine, 100 U/ml penicillin, 100 μg/ml streptomycin, 0.05 mM 2-mercaptoethanol, and 1 µg/ml dextrose) (TCM) plus 5% human serum and washed twice in TCM.

The PBMC were then activated to form lymphoblasts. In particular, 0.5–1×10$^6$ cells/ml in TCM plus 5% human serum plus 0.1% (v/v) PHA-P (Difco, Detroit, Mich.) were cultured for 3 days at 37° C. in a 5% CO$_2$ atmosphere.

After three days, cell cultures were split 1:1 by volume in TCM plus 5% human serum and 50 U/ml recombinant human IL-2 to yield >95% T-cells. These cells were utilized for preparation of a cDNA library.

EXAMPLE 2
Extraction and characterization of RNA

PBMC isolated as in Example 1, activated with PHA for 2–3 days, were harvested and total RNA was extracted using Guanidine Isothiocyanate/Phenol as described by P. Chomczynski and N. Sacchi, Anal. Biochem., 162:156, 1987. PolyA$^+$ RNA was isolated from the total RNA by one batch adsorption to oligo dT latex beads as described (K. Kuribayashi et al., Nucl. Acids Res. Symposium Series 19:61, 1988). The mass yield of this purification was about 4% of polyA+ RNA.

EXAMPLE 3
cDNA library

From the above polyA$^+$ RNA, a cDNA library was established in the mammalian expression vector pEF-BOS as follows.

3 µg of polyA$^+$ RNA were reverse transcribed into single stranded cDNAs using RNaseH minus reverse transcriptase in the presence of α-$^{32}$P-dCTP. The resulting single stranded cDNAs were converted into blunt ended double stranded cDNAs as described by U. Gubler and A. Chua, Essential Molecular Biology Volume II, T. A. Brown, editor, pp. 39–56, IRL Press 1991. BstXI linkers (A. Aruffo and B. Seed, Proc. Natl. Acad. Sci (USA) 84, 8573, 1987) were ligated to the resulting double stranded cDNAs.

cDNA molecules having a size of greater than 800 base pairs (bp) were selected by size exclusion chromatography as follows. A Sephacryl SF 500 column (0.8×29 cm) was packed by gravity in 10 mM Tris-HCl pH 7.8–1 mM EDTA-100 mM NaAcetate. The radioactive cDNA with added BstXI linkers was applied to the column and 0.5 ml fractions were collected. The size distribution of radioactive cDNA was determined by performing electrophoresis on a small aliquot of each fraction on a 1% agarose gel, drying the gel, and visualizing the size by exposure of the gel to X-ray film. cDNA molecules larger than 800 bp were size selected in this fashion.

The selected cDNA molecules were pooled and concentrated by ethanol precipitation. The pooled and concentrated selected cDNA molecules were subsequently ligated to the plasmid pEF-BOS as follows. The plasmid had been restricted with BstXI and purified over two consecutive 1% agarose gels. 300 ng of the restricted and purified plasmid DNA were ligated to 30 ng of size selected cDNA in 60 µl of ligation buffer (50 mM Tris-HCl pH 7.8–10 mM MgCl$_2$-10 mM DT-1 mM rATP-25 mg/ml BSA) at 15° C. overnight.

The following day, the plasmid ligated with the size selected cDNA was extracted with phenol. 6 mg of mussel glycogen were added to the resulting extract, and the nucleic acids were precipitated by ethanol. The resulting precipitate was dissolved in water and the nucleic acids again were precipitated by ethanol, followed by a wash with 80% ethanol. A pellet was formed from the precipitated and washed nucleic acids. The pellet was dissolved in 6 µl of water. 1 µl aliquots of the dissolved pellet were subsequently electroporated into *E. Coli* strain DH-10B. Upon electroporation of 5 parallel aliquots, a library of about 10 million recombinants was generated.

EXAMPLE 4
Expression Screening for cDNAs encoding high affinity IL-12 receptors The library was screened according to the general expression screening method described by Hara and Miyajima, 1992, EMBO, 11:1875.

Pools of about 100 *E. coli* clones from the above library were grown and the plasmid DNA was extracted from the pools by conventional methods. 2×10$^5$ COS cells were plated per 35 mm culture well. COS cells were transfected with a transfection cocktail using the standard DEAE dextran technique described in "Molecular Cloning, a Laboratory Manual", 2nd Ed., J. Sambrook et al., Cold Spring Harbor Laboratory Press, 1989 ("Molecular Cloning"). The transfection cocktail contained (1) 1 µg of plasmid DNA extracted from the *E. Coli* clone pools derived from the above library, and (2) 0.1 µg of pEF-BOS plasmid DNA containing the human IL-12 receptor beta1 cDNA.

3 days after transfection, the wells of COS cells were incubated with 10 pM labeled human recombinant IL-12 (specific activity=1000–2000 cpm/fmole) for 90 minutes at room temperature. The labeled human recombinant IL-12 was removed, and the COS cell monolayer was washed for one hour three times with binding buffer (RPMI 1640, 5% fetal bovine serum (FBS), 25 mM HEPES pH 7) to further select for COS cells expressing high affinity IL-12 receptors only (the binding of the IL-12 ligand to the low affinity sites was further reduced because the low affinity sites have a higher dissociation rate). Subsequently, the cell monolayers were lysed and counted in a gamma counter. After screening 440 pools (representing about 44,000 clones), one pool consistently showed a positive binding signal (300 cpm over 100 cpm background). From this pool, a single clone was subsequently isolated by sib-selection. This single clone (B5-10) contained a cDNA insert of about 3 kb that was completely sequenced.

The cDNA insert of clone B5-10 was incomplete with regard to the protein coding region because it did not contain an in-frame stop codon. The cDNA library of Example 3 was rescreened by conventional DNA hybridization techniques with the cDNA insert from clone B5-10, as described in Molecular Cloning and by Grunstein and Hogness, 1975, Proc. Nat. Acad. Sci. USA., 72:3961. Additional clones were thus isolated and then partially sequenced. The nucleotide sequence of one clone (No. 3) was found to (i) overlap with the 3' end of the nucleotide sequence of clone B5-10, (ii) extend beyond the nucleotide sequence of clone B5-10, and (iii) contain an in-frame stop codon.

This composite DNA sequence is shown in (SEQ ID NO:1). The deduced amino acid sequence for the encoded receptor protein is shown in SEQ ID NO:2. Based on the previously suggested nomenclature of Stahl and Yancopolous, 1993, Cell 74:587, we call this newly isolated human IL-12 receptor chain the beta2 chain.

EXAMPLE 5
Binding Assays

COS cells (4–5×10$^7$) were transfected by electroporation using a BioRad Gene Pulser (250 µF, 250 volts) with either (1) 25 µg of the B5-10 plasmid DNA expressing recombinant human IL-12 beta2 receptor protein, (2) 25 µg of the pEF-BOS plasmid DNA expressing recombinant human IL-12 beta1 receptor protein, or (3) a mixture of 12.5 µg of the B5-10 plasmid DNA expressing recombinant human IL-12 beta2 receptor protein and 12.5 µg of the pEF-BOS plasmid DNA expressing recombinant human IL-12 beta1 receptor protein. The electroporated cells were plated in a 600 cm² culture plate, harvested after 72 hours by scraping, washed and resuspended in binding buffer.

The cells were assayed to determine affinities of the expressed IL-12 receptors for human IL-12. In particular, equilibrium binding of labeled recombinant human IL-12 to the cells was performed and analyzed as described by R. Chizzonite, et al., 1992, J. Immunol., 148:3117. Electroporated cells ($8 \times 10^4$) were incubated with increasing concentrations of $^{125}$I-labeled recombinant human IL-12 at room temperature for 2 hours. Incubations were carried out in duplicate or triplicate.

Cell bound radioactivity was separated from free labeled $^{125}$I-IL-12 by centrifugation of the mixture of electroporated cells and $^{125}$I-labeled recombinant human IL-12 through 0.1 ml of an oil mixture (1:2 mixture of Thomas Silicone Fluid 6428-R15 {A. H. Thomas} and Silicone Oil AR 200 {Gallard-Schlessinger}) at 4° C. for 90 seconds at 10,000×g to form a cell pellet in a tube. The cell pellet was excised from the tip of the tube in which it was formed, and cell bound radioactivity was determined in a gamma counter.

Receptor binding data were analyzed and the affinities were calculated according to Scatchard using the method described by McPherson, J., 1985, Pharmacol. Methods, 14:213.

EXAMPLE 6
Production of IL-12 responsive cell line

Wild-type Ba/F3 cells, an IL-3-dependent mouse pro-B cell (Palacios, R. et al., 1985, Cell 41:727) and Ba/F3 cells expressing human IL-12 beta1 receptor protein (Chua, A., et al., 1994, J. Imunology 153:128) were cotransfected with (1) 80 μg of pEF-BOS plasmid DNA expressing recombinant human IL-12 beta2 receptor protein and (2) 8 μg of a plasmid expressing a hygromycin resistance gene (Giordano, T. J., et al., 1990, Gene 88:285) by electroporation using a BioRad Gene Pulser (960 μF, 400 volts).

All cells were resuspended at a density of $2 \times 10^5$ viable cells/ml in a growth medium of RPMI 1640, 10% FBS, glutamine (2 mM), penicillin G (100 U/ml), streptomycin (100 μg/ml), and 10% conditioned medium from the WEHI-3 cell line (ATCC No. TIB 68, American Type Culture Collection, Rockville, Md). The WEHI-3 cell line is a source of IL-3. The resuspended cells were then incubated at 37° C. under 5% $CO_2$ for 120 hours.

Cells were selected by their ability to grow in (1) the above growth medium in the presence of 1 mg/ml hygromycin or (2) an IL-12 containing growth medium of RPMI 1640, 10% FBS, glutamine (2mM), penicillin G (100 U/ml), streptomycin (100 μg/ml), and various concentrations (10, 50 or 250 ng/ml) of human IL-12.

Ba/F3 cells expressing human IL-12 beta1 receptor protein transfected with pEF-BOS plasmid DNA expressing recombinant human IL-12 beta2 receptor protein grew in the IL-12 containing growth medium, demonstrating that coexpression of human IL-12 beta1 receptor protein and human IL-12 beta2 receptor protein conferred human IL-12 responsiveness to the Ba/F3 cells.

Additionally, Ba/F3 cells expressing human IL-12 beta2 receptor protein grow in the IL-12 containing growth medium, demonstrating that expression of human IL-12 beta2 receptor protein conferred human IL-12 responsiveness to the Ba/F3 cells.

Effect of human IL-12 on transfected Ba/F3 cell lines

Ba/F3 cells (1) expressing human IL-12 beta1 receptor protein, (2) expressing human IL-12 beta2 receptor protein, or (3) coexpressing human IL-12 beta1 receptor protein and human IL-12 beta2 receptor protein were cultured in RPMI-1640 medium supplemented with 10% FBS, 100 U/ml penicillin G, 100 μg/ml streptomycin, and 2 mM L-glutamine at $2 \times 10^4$ cells/well in Costar 3596 flat-bottom microplates for 24 hours. Various dilutions of human IL-12, as shown in FIG. 6, were then added to the microplates and the cells were incubated for 42 hours at 37° C. in a humidified atmosphere of 5% $CO_2$ in air. 50 μl of $^3$H-thymidine, 10 μCi/ml in culture medium, was then added to each well. The cultures were further incubated for 6 hours at 37° C. Subsequently, the culture contents were harvested onto glass fiber filters by means of a cell harvester. $^3$H-thymidine incorporation was measured by use of a liquid scintillation counter. All samples were assayed in quadruplicate.

RESULTS
Sequence Analysis of IL-12 receptor cDNA clones and encoded IL-12 receptor protein The IL-12 beta2 receptor protein, composed of 862 amino acids and a calculated molecular weight of 97231, had the following features: N-terminal signal peptide, extracellular domain, transmembrane domain and cytoplasmic tail. The classical hydrophobic N-terminal signal peptide is predicted to be 23 amino acids in length. Signal peptide cleavage occurs mostly after the amino acids Ala, Ser, Gly, Cys, Thr, Gln (von Heijne, G., 1986, Nucl. Acids Research, 14:4683). For the IL-12 receptor, the cleavage could thus take place after Ala23 in the sequence shown in SEQ ID NO:2, leaving a mature protein of 839 amino acids based on cleavage at Ala23. The extracellular domain of the receptor is predicted to encompass the region from the C-terminus of the signal peptide to amino acid No. 622 in the sequence shown in SEQ ID NO:2. Hydrophobicity analysis shows the area from amino acid No. 623 to 646 to be hydrophobic, as would be expected for a transmembrane anchor region. Charged transfer stop residues can be found at the N- as well as the C-terminus of this predicted transmembrane area. The extracellular domain of the receptor is thus 599 amino acids long and contains 9 predicted N-linked glycosylation sites. The cytoplasmic portion is 215 amino acids long (amino acid residue nos. 647 to 862).

Further analysis of the amino acid sequence shown in SEQ ID NO:2 shows the human IL-12 beta2 receptor protein is a member of the cytokine receptor superfamily, by virtue of the sequence motifs [Cys132 - - - Cys143TW] and [W305SKWS]. Comparing the sequence shown in SEQ ID NO:2 to all the members of the superfamily by running the ALIGN program shows that the human IL-12 beta2 receptor protein has the highest homology to human gp130. The cytoplasmic region of the IL-12 receptor beta2 chain contains the box 1 and 2 motifs found in other cytokine receptor superfamily members, as well as three tyrosine residues. Phosphorylation of tyrosines is commonly associated with cytokine receptor signalling; the presence of these tyrosine residues underscores the importance of the IL-12 receptor beta2 chain in the formation of a functional IL-12 receptor. The IL-12 receptor beta1 chain does not contain any tyrosine residues in its cytoplasmic tail.

Binding Assays

We have found that human IL-12 binds to recombinant IL-12 receptor beta1 or beta2 alone with an apparent affinity of about 2–5 nM. The binding data was described by a single site receptor model, corresponding to the low affinity component of the functional IL-12 receptor found on PHA-activated PBMC (R. Chizzonite et al., 1992, J. Immunol., 148:3117; B. Desai et al., 1992, J. Immunol., 148:3125).

In contrast to these results, both high and low affinity IL-12 binding sites were generated upon cotransfection of COS cells with IL-12 receptor beta1 and beta2 plasmids. In this case, the binding data were described by a two receptor site model, with affinities of 50 pM and 5 nM.

Effect of human IL-12 on transfected Ba/F3 cell lines

The results of the proliferation assay for the effect of human IL-12 on Ba/F3 cells (1) expressing human IL-12 beta1 receptor protein, (2) expressing human IL-12 beta2 receptor protein, and (3) coexpressing human IL-12 beta1 receptor protein and human IL-12 beta2 receptor protein.

We have found that cells that are transfected with cDNAs for both human IL-12 beta1 receptor protein and human IL-12 beta2 receptor protein respond to stimulation by human IL-12 by proliferating in a dose-dependent manner.

Additionally, cells we have found that are transfected with cDNAs for human IL-12 beta2 receptor protein respond to stimulation by human IL-12 by proliferating in a dose-dependent manner.

Conclusion:

The isolated cDNA (clone No. B5-10, SEQ.ID. No:1) coding for a type I transmembrane protein represents a second component of the IL-12 receptor (IL-12R beta2) found on normal human T-cells. The beta1 and beta2 chains each alone bind IL-12 only with low affinity (Kd=2–5 nM). Upon coexpression of beta1 and beta2, two affinity sites are observed, with Kd values of 50 pM and 5 nM.

Ba/F3 cells expressing human IL-12 beta2 receptor protein or coexpressing human IL-12 beta1 receptor protein and human IL-12 beta2 receptor protein are responsive to human IL-12.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An antibody directed against a interleukin-12 (IL-12) beta2 receptor protein which protein (a) has low binding affinity for human IL-12, and (b) when complexed with a human IL-12 beta1 receptor protein forms a complex having high binding affinity to human IL-12.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4040 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 641..3226

( x i ) SEQUENCE DESCRIPTION: SEQ ID NO:1:

```
TGCAGAGAAC  AGAGAAAGGA  CATCTGCGAG  GAAAGTTCCC  TGATGGCTGT  CAACAAAGTG         60

CCACGTCTCT  ATGGCTGTGT  ACGCTGAGCA  CACGATTTTA  TCGCGCCTAT  CATATCTTGG        120

TGCATAAACG  CACCTCACCT  CGGTCAACCC  TTGCTCCGTC  TTATGAGACA  GGCTTTATTA        180

TCCGCATTTT  ATATGAGGGG  AATCTGACGG  TGGAGAGAGA  ATTATCTTGC  TCAAGGCGAC        240

ACAGCAGAGC  CCACAGGTGG  CAGAATCCCA  CCCGAGCCCG  CTTCGACCCG  CGGGGTGGAA        300

ACCACGGGCG  CCCGCCCGGC  TGCGCTTCCA  GAGCTGAACT  GAGAAGCGAG  TCCTCTCCGC        360

CCTGCGGCCA  CCGCCCAGCC  CCGACCCCCG  CCCCGGCCCG  ATCCTCACTC  GCCGCCAGCT        420

CCCCGCGCCC  ACCCCGGAGT  TGGTGGCGCA  GAGGCGGGAG  GCGGAGGCGG  GAGGGCGGGC        480

GCTGGCACCG  GGAACGCCCG  AGCGCCGGCA  GAGAGCGCGG  AGAGCGCGAC  ACGTGCGGCC        540

CAGAGCACCG  GGGCCACCCG  GTCCCCGCAG  GCCCGGGACC  GCGCCCGCTG  GCAGGCGACA        600

CGTGGAAGAA  TACGGAGTTC  TATACCAGAG  TTGATTGTTG  ATG GCA CAT ACT TTT          655
                                                  Met Ala His Thr Phe
                                                   1               5

AGA GGA TGC TCA TTG GCA TTT ATG TTT ATA ATC ACG TGG CTG TTG ATT            703
Arg Gly Cys Ser Leu Ala Phe Met Phe Ile Ile Thr Trp Leu Leu Ile
```

```
          10                         15                           20
AAA  GCA  AAA  ATA  GAT  GCG  TGC  AAG  AGA  GGC  GAT  GTG  ACT  GTG  AAG  CCT        751
Lys  Ala  Lys  Ile  Asp  Ala  Cys  Lys  Arg  Gly  Asp  Val  Thr  Val  Lys  Pro
               25                   30                   35

TCC  CAT  GTA  ATT  TTA  CTT  GGA  TCC  ACT  GTC  AAT  ATT  ACA  TGC  TCT  TTG        799
Ser  His  Val  Ile  Leu  Leu  Gly  Ser  Thr  Val  Asn  Ile  Thr  Cys  Ser  Leu
          40                        45                        50

AAG  CCC  AGA  CAA  GGC  TGC  TTT  CAC  TAT  TCC  AGA  CGT  AAC  AAG  TTA  ATC        847
Lys  Pro  Arg  Gln  Gly  Cys  Phe  His  Tyr  Ser  Arg  Arg  Asn  Lys  Leu  Ile
     55                        60                        65

CTG  TAC  AAG  TTT  GAC  AGA  AGA  ATC  AAT  TTT  CAC  CAT  GGC  CAC  TCC  CTC        895
Leu  Tyr  Lys  Phe  Asp  Arg  Arg  Ile  Asn  Phe  His  His  Gly  His  Ser  Leu
70                        75                        80                        85

AAT  TCT  CAA  GTC  ACA  GGT  CTT  CCC  CTT  GGT  ACA  ACC  TTG  TTT  GTC  TGC        943
Asn  Ser  Gln  Val  Thr  Gly  Leu  Pro  Leu  Gly  Thr  Thr  Leu  Phe  Val  Cys
                    90                        95                        100

AAA  CTG  GCC  TGT  ATC  AAT  AGT  GAT  GAA  ATT  CAA  ATA  TGT  GGA  GCA  GAG        991
Lys  Leu  Ala  Cys  Ile  Asn  Ser  Asp  Glu  Ile  Gln  Ile  Cys  Gly  Ala  Glu
               105                       110                       115

ATC  TTC  GTT  GGT  GTT  GCT  CCA  GAA  CAG  CCT  CAA  AAT  TTA  TCC  TGC  ATA       1039
Ile  Phe  Val  Gly  Val  Ala  Pro  Glu  Gln  Pro  Gln  Asn  Leu  Ser  Cys  Ile
          120                       125                       130

CAG  AAG  GGA  GAA  CAG  GGG  ACT  GTG  GCC  TGC  ACC  TGG  GAA  AGA  GGA  CGA       1087
Gln  Lys  Gly  Glu  Gln  Gly  Thr  Val  Ala  Cys  Thr  Trp  Glu  Arg  Gly  Arg
     135                       140                       145

GAC  ACC  CAC  TTA  TAC  ACT  GAG  TAT  ACT  CTA  CAG  CTA  AGT  GGA  CCA  AAA       1135
Asp  Thr  His  Leu  Tyr  Thr  Glu  Tyr  Thr  Leu  Gln  Leu  Ser  Gly  Pro  Lys
150                       155                       160                       165

AAT  TTA  ACC  TGG  CAG  AAG  CAA  TGT  AAA  GAC  ATT  TAT  TGT  GAC  TAT  TTG       1183
Asn  Leu  Thr  Trp  Gln  Lys  Gln  Cys  Lys  Asp  Ile  Tyr  Cys  Asp  Tyr  Leu
                    170                       175                       180

GAC  TTT  GGA  ATC  AAC  CTC  ACC  CCT  GAA  TCA  CCT  GAA  TCC  AAT  TTC  ACA       1231
Asp  Phe  Gly  Ile  Asn  Leu  Thr  Pro  Glu  Ser  Pro  Glu  Ser  Asn  Phe  Thr
               185                       190                       195

GCC  AAG  GTT  ACT  GCT  GTC  AAT  AGT  CTT  GGA  AGC  TCC  TCT  TCA  CTT  CCA       1279
Ala  Lys  Val  Thr  Ala  Val  Asn  Ser  Leu  Gly  Ser  Ser  Ser  Ser  Leu  Pro
          200                       205                       210

TCC  ACA  TTC  ACA  TTC  TTG  GAC  ATA  GTG  AGG  CCT  CTT  CCT  CCG  TGG  GAC       1327
Ser  Thr  Phe  Thr  Phe  Leu  Asp  Ile  Val  Arg  Pro  Leu  Pro  Pro  Trp  Asp
     215                       220                       225

ATT  AGA  ATC  AAA  TTT  CAA  AAG  GCT  TCC  GTG  AGC  AGA  TGT  ACC  CTT  TAT       1375
Ile  Arg  Ile  Lys  Phe  Gln  Lys  Ala  Ser  Val  Ser  Arg  Cys  Thr  Leu  Tyr
230                       235                       240                       245

TGG  AGA  GAT  GAG  GGA  CTG  GTA  CTG  CTT  AAT  CGA  CTC  AGA  TAT  CGG  CCC       1423
Trp  Arg  Asp  Glu  Gly  Leu  Val  Leu  Leu  Asn  Arg  Leu  Arg  Tyr  Arg  Pro
                    250                       255                       260

AGT  AAC  AGC  AGG  CTC  TGG  AAT  ATG  GTT  AAT  GTT  ACA  AAG  GCC  AAA  GGA       1471
Ser  Asn  Ser  Arg  Leu  Trp  Asn  Met  Val  Asn  Val  Thr  Lys  Ala  Lys  Gly
               265                       270                       275

AGA  CAT  GAT  TTG  CTG  GAT  CTG  AAA  CCA  TTT  ACA  GAA  TAT  GAA  TTT  CAG       1519
Arg  His  Asp  Leu  Leu  Asp  Leu  Lys  Pro  Phe  Thr  Glu  Tyr  Glu  Phe  Gln
          280                       285                       290

ATT  TCC  TCT  AAG  CTA  CAT  CTT  TAT  AAG  GGA  AGT  TGG  AGT  GAT  TGG  AGT       1567
Ile  Ser  Ser  Lys  Leu  His  Leu  Tyr  Lys  Gly  Ser  Trp  Ser  Asp  Trp  Ser
     295                       300                       305

GAA  TCA  TTG  AGA  GCA  CAA  ACA  CCA  GAA  GAA  GAG  CCT  ACT  GGG  ATG  TTA       1615
Glu  Ser  Leu  Arg  Ala  Gln  Thr  Pro  Glu  Glu  Glu  Pro  Thr  Gly  Met  Leu
310                       315                       320                       325

GAT  GTC  TGG  TAC  ATG  AAA  CGG  CAC  ATT  GAC  TAC  AGT  AGA  CAA  CAG  ATT       1663
Asp  Val  Trp  Tyr  Met  Lys  Arg  His  Ile  Asp  Tyr  Ser  Arg  Gln  Gln  Ile
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 330 |     |     |     |     | 335 |     |     |     |     | 340 |     |      |
| TCT | CTT | TTC | TGG | AAG | AAT | CTG | AGT | GTC | TCA | GAG | GCA | AGA | GGA | AAA | ATT | 1711 |
| Ser | Leu | Phe | Trp | Lys | Asn | Leu | Ser | Val | Ser | Glu | Ala | Arg | Gly | Lys | Ile |      |
|     |     |     | 345 |     |     |     |     | 350 |     |     |     |     | 355 |     |     |      |
| CTC | CAC | TAT | CAG | GTG | ACC | TTG | CAG | GAG | CTG | ACA | GGA | GGG | AAA | GCC | ATG | 1759 |
| Leu | His | Tyr | Gln | Val | Thr | Leu | Gln | Glu | Leu | Thr | Gly | Gly | Lys | Ala | Met |      |
|     |     | 360 |     |     |     |     | 365 |     |     |     |     | 370 |     |     |     |      |
| ACA | CAG | AAC | ATC | ACA | GGA | CAC | ACC | TCC | TGG | ACC | ACA | GTC | ATT | CCT | AGA | 1807 |
| Thr | Gln | Asn | Ile | Thr | Gly | His | Thr | Ser | Trp | Thr | Thr | Val | Ile | Pro | Arg |      |
|     | 375 |     |     |     |     | 380 |     |     |     |     | 385 |     |     |     |     |      |
| ACC | GGA | AAT | TGG | GCT | GTG | GCT | GTG | TCT | GCA | GCA | AAT | TCA | AAA | GGC | AGT | 1855 |
| Thr | Gly | Asn | Trp | Ala | Val | Ala | Val | Ser | Ala | Ala | Asn | Ser | Lys | Gly | Ser |      |
| 390 |     |     |     |     | 395 |     |     |     |     | 400 |     |     |     |     | 405 |      |
| TCT | CTG | CCC | ACT | CGT | ATT | AAC | ATA | ATG | AAC | CTG | TGT | GAG | GCA | GGG | TTG | 1903 |
| Ser | Leu | Pro | Thr | Arg | Ile | Asn | Ile | Met | Asn | Leu | Cys | Glu | Ala | Gly | Leu |      |
|     |     |     |     | 410 |     |     |     |     | 415 |     |     |     |     | 420 |     |      |
| CTG | GCT | CCT | CGC | CAG | GTC | TCT | GCA | AAC | TCA | GAG | GGC | ATG | GAC | AAC | ATT | 1951 |
| Leu | Ala | Pro | Arg | Gln | Val | Ser | Ala | Asn | Ser | Glu | Gly | Met | Asp | Asn | Ile |      |
|     |     |     | 425 |     |     |     |     | 430 |     |     |     |     | 435 |     |     |      |
| CTG | GTG | ACT | TGG | CAG | CCT | CCC | AGG | AAA | GAT | CCC | TCT | GCT | GTT | CAG | GAG | 1999 |
| Leu | Val | Thr | Trp | Gln | Pro | Pro | Arg | Lys | Asp | Pro | Ser | Ala | Val | Gln | Glu |      |
|     |     | 440 |     |     |     |     | 445 |     |     |     |     | 450 |     |     |     |      |
| TAC | GTG | GTG | GAA | TGG | AGA | GAG | CTC | CAT | CCA | GGG | GGT | GAC | ACA | CAG | GTC | 2047 |
| Tyr | Val | Val | Glu | Trp | Arg | Glu | Leu | His | Pro | Gly | Gly | Asp | Thr | Gln | Val |      |
|     | 455 |     |     |     |     | 460 |     |     |     |     | 465 |     |     |     |     |      |
| CCT | CTA | AAC | TGG | CTA | CGG | AGT | CGA | CCC | TAC | AAT | GTG | TCT | GCT | CTG | ATT | 2095 |
| Pro | Leu | Asn | Trp | Leu | Arg | Ser | Arg | Pro | Tyr | Asn | Val | Ser | Ala | Leu | Ile |      |
| 470 |     |     |     |     | 475 |     |     |     |     | 480 |     |     |     |     | 485 |      |
| TCA | GAG | AAC | ATA | AAA | TCC | TAC | ATC | TGT | TAT | GAA | ATC | CGT | GTG | TAT | GCA | 2143 |
| Ser | Glu | Asn | Ile | Lys | Ser | Tyr | Ile | Cys | Tyr | Glu | Ile | Arg | Val | Tyr | Ala |      |
|     |     |     |     | 490 |     |     |     |     | 495 |     |     |     |     | 500 |     |      |
| CTC | TCA | GGG | GAT | CAA | GGA | GGA | TGC | AGC | TCC | ATC | CTG | GGT | AAC | TCT | AAG | 2191 |
| Leu | Ser | Gly | Asp | Gln | Gly | Gly | Cys | Ser | Ser | Ile | Leu | Gly | Asn | Ser | Lys |      |
|     |     |     | 505 |     |     |     |     | 510 |     |     |     |     | 515 |     |     |      |
| CAC | AAA | GCA | CCA | CTG | AGT | GGC | CCC | CAC | ATT | AAT | GCC | ATC | ACA | GAG | GAA | 2239 |
| His | Lys | Ala | Pro | Leu | Ser | Gly | Pro | His | Ile | Asn | Ala | Ile | Thr | Glu | Glu |      |
|     |     | 520 |     |     |     |     | 525 |     |     |     |     | 530 |     |     |     |      |
| AAG | GGG | AGC | ATT | TTA | ATT | TCA | TGG | AAC | AGC | ATT | CCA | GTC | CAG | GAG | CAA | 2287 |
| Lys | Gly | Ser | Ile | Leu | Ile | Ser | Trp | Asn | Ser | Ile | Pro | Val | Gln | Glu | Gln |      |
|     |     |     |     | 535 |     |     |     |     | 540 |     |     |     |     | 545 |     |      |
| ATG | GGC | TGC | CTC | CTC | CAT | TAT | AGG | ATA | TAC | TGG | AAG | GAA | CGG | GAC | TCC | 2335 |
| Met | Gly | Cys | Leu | Leu | His | Tyr | Arg | Ile | Tyr | Trp | Lys | Glu | Arg | Asp | Ser |      |
| 550 |     |     |     |     | 555 |     |     |     |     | 560 |     |     |     |     | 565 |      |
| AAC | TCC | CAG | CCT | CAG | CTC | TGT | GAA | ATT | CCC | TAC | AGA | GTC | TCC | CAA | AAT | 2383 |
| Asn | Ser | Gln | Pro | Gln | Leu | Cys | Glu | Ile | Pro | Tyr | Arg | Val | Ser | Gln | Asn |      |
|     |     |     |     | 570 |     |     |     |     | 575 |     |     |     |     | 580 |     |      |
| TCA | CAT | CCA | ATA | AAC | AGC | CTG | CAG | CCC | CGA | GTG | ACA | TAT | GTC | CTG | TGG | 2431 |
| Ser | His | Pro | Ile | Asn | Ser | Leu | Gln | Pro | Arg | Val | Thr | Tyr | Val | Leu | Trp |      |
|     |     |     | 585 |     |     |     |     | 590 |     |     |     |     | 595 |     |     |      |
| ATG | ACA | GCT | CTG | ACA | GCT | GCT | GGT | GAA | AGT | TCC | CAC | GGA | AAT | GAG | AGG | 2479 |
| Met | Thr | Ala | Leu | Thr | Ala | Ala | Gly | Glu | Ser | Ser | His | Gly | Asn | Glu | Arg |      |
|     |     | 600 |     |     |     |     | 605 |     |     |     |     | 610 |     |     |     |      |
| GAA | TTT | TGT | CTG | CAA | GGT | AAA | GCC | AAT | TGG | ATG | GCG | TTT | GTG | GCA | CCA | 2527 |
| Glu | Phe | Cys | Leu | Gln | Gly | Lys | Ala | Asn | Trp | Met | Ala | Phe | Val | Ala | Pro |      |
|     | 615 |     |     |     |     | 620 |     |     |     |     | 625 |     |     |     |     |      |
| AGC | ATT | TGC | ATT | GCT | ATC | ATC | ATG | GTG | GGC | ATT | TTC | TCA | ACG | CAT | TAC | 2575 |
| Ser | Ile | Cys | Ile | Ala | Ile | Ile | Met | Val | Gly | Ile | Phe | Ser | Thr | His | Tyr |      |
| 630 |     |     |     |     | 635 |     |     |     |     | 640 |     |     |     |     | 645 |      |
| TTC | CAG | CAA | AAG | GTG | TTT | GTT | CTC | CTA | GCA | GCC | CTC | AGA | CCT | CAG | TGG | 2623 |
| Phe | Gln | Gln | Lys | Val | Phe | Val | Leu | Leu | Ala | Ala | Leu | Arg | Pro | Gln | Trp |      |

```
                          650                           655                           660
TGT  AGC  AGA  GAA  ATT  CCA  GAT  CCA  GCA  AAT  AGC  ACT  TGC  GCT  AAG  AAA         2671
Cys  Ser  Arg  Glu  Ile  Pro  Asp  Pro  Ala  Asn  Ser  Thr  Cys  Ala  Lys  Lys
               665                      670                      675

TAT  CCC  ATT  GCA  GAG  GAG  AAG  ACA  CAG  CTG  CCC  TTG  GAC  AGG  CTC  CTG         2719
Tyr  Pro  Ile  Ala  Glu  Glu  Lys  Thr  Gln  Leu  Pro  Leu  Asp  Arg  Leu  Leu
               680                      685                      690

ATA  GAC  TGG  CCC  ACG  CCT  GAA  GAT  CCT  GAA  CCG  CTG  GTC  ATC  AGT  GAA         2767
Ile  Asp  Trp  Pro  Thr  Pro  Glu  Asp  Pro  Glu  Pro  Leu  Val  Ile  Ser  Glu
          695                      700                      705

GTC  CTT  CAT  CAA  GTG  ACC  CCA  GTT  TTC  AGA  CAT  CCC  CCC  TGC  TCC  AAC         2815
Val  Leu  His  Gln  Val  Thr  Pro  Val  Phe  Arg  His  Pro  Pro  Cys  Ser  Asn
710                      715                      720                           725

TGG  CCA  CAA  AGG  GAA  AAA  GGA  ATC  CAA  GGT  CAT  CAG  GCC  TCT  GAG  AAA         2863
Trp  Pro  Gln  Arg  Glu  Lys  Gly  Ile  Gln  Gly  His  Gln  Ala  Ser  Glu  Lys
                    730                      735                      740

GAC  ATG  ATG  CAC  AGT  GCC  TCA  AGC  CCA  CCA  CCT  CCA  AGA  GCT  CTC  CAA         2911
Asp  Met  Met  His  Ser  Ala  Ser  Ser  Pro  Pro  Pro  Pro  Arg  Ala  Leu  Gln
               745                      750                      755

GCT  GAG  AGC  AGA  CAA  CTG  GTG  GAT  CTG  TAC  AAG  GTG  CTG  GAG  AGC  AGG         2959
Ala  Glu  Ser  Arg  Gln  Leu  Val  Asp  Leu  Tyr  Lys  Val  Leu  Glu  Ser  Arg
          760                      765                      770

GGC  TCC  GAC  CCA  AAG  CCA  GAA  AAC  CCA  GCC  TGT  CCC  TGG  ACG  GTG  CTC         3007
Gly  Ser  Asp  Pro  Lys  Pro  Glu  Asn  Pro  Ala  Cys  Pro  Trp  Thr  Val  Leu
          775                      780                      785

CCA  GCA  GGT  GAC  CTT  CCC  ACC  CAT  GAT  GGC  TAC  TTA  CCC  TCC  AAC  ATA         3055
Pro  Ala  Gly  Asp  Leu  Pro  Thr  His  Asp  Gly  Tyr  Leu  Pro  Ser  Asn  Ile
790                      795                      800                           805

GAT  GAC  CTC  CCC  TCA  CAT  GAG  GCA  CCT  CTC  GCT  GAC  TCT  CTG  GAA  GAA         3103
Asp  Asp  Leu  Pro  Ser  His  Glu  Ala  Pro  Leu  Ala  Asp  Ser  Leu  Glu  Glu
               810                      815                      820

CTG  GAG  CCT  CAG  CAC  ATC  TCC  CTT  TCT  GTT  TTC  CCC  TCA  AGT  TCT  CTT         3151
Leu  Glu  Pro  Gln  His  Ile  Ser  Leu  Ser  Val  Phe  Pro  Ser  Ser  Ser  Leu
               825                      830                      835

CAC  CCA  CTC  ACC  TTC  TCC  TGT  GGT  GAT  AAG  CTG  ACT  CTG  GAT  CAG  TTA         3199
His  Pro  Leu  Thr  Phe  Ser  Cys  Gly  Asp  Lys  Leu  Thr  Leu  Asp  Gln  Leu
               840                      845                      850

AAG  ATG  AGG  TGT  GAC  TCC  CTC  ATG  CTC  TGAGTGGTGA GGCTTCAAGC                      3246
Lys  Met  Arg  Cys  Asp  Ser  Leu  Met  Leu
               855                      860

CTTAAAGTCA GTGTGCCCTC AACCAGCACA GCCTGCCCCA ATTCCCCCAG CCCCTGCTCC                       3306
AGCAGCTGTC ATCTCTGGGT GCCACCATCG GTCTGGCTGC AGCTAGAGGA CAGGCAAGCC                       3366
AGCTCTGGGG GAGTCTTAGG AACTGGGAGT TGGTCTTCAC TCAGATGCCT CATCTTGCCT                       3426
TTCCCAGGGC CTTAAAATTA CATCCTTCAC TGTGTGGACC TAGAGACTCC AACTTGAATT                       3486
CCTAGTAACT TTCTTGGTAT GCTGGCCAGA AAGGGAAATG AGGAGGAGAG TAGAAACCAC                       3546
AGCTCTTAGT AGTAATGGCA TACAGTCTAG AGGACCATTC ATGCAATGAC TATTTCTAAA                       3606
GCACCTGCTA CACAGCAGGC TGTACACAGC AGATCAGTAC TGTTAACAG AACTTCCTGA                        3666
GATGATGGAA ATGTTCTACC TCTGCACTCA CTGTCCAGTA CATTAGACAC TAGGCACATT                       3726
GGCTGTTAAT CACTTGGAAT GTGTTTAGCT TGACTGAGGA ATTAAATTTT GATTGTAAAT                       3786
TTAAATCGCC ACACATGGCT AGTGGCTACT GTATTGGAGT GCACAGCTCT AGATGGCTCC                       3846
TAGATTATTG AGAGCCTCCA AAACAAATCA ACCTAGTTCT ATAGATGAAG ACATAAAAGA                       3906
CACTGGTAAA CACCAATGTA AAAGGGCCCC CAAGGTGGTC ATGACTGGTC TCATTTGCAG                       3966
AAGTCTAAGA ATGTACCTTT TTCTGGCCGG GCGTGGTAGC TCATGCCTGT AATCCCAGCA                       4026
```

CTTTGGGAGG CTGA 4040

( 2 ) INFORMATION FOR SEQ ID NO:2:

( i ) SEQUENCE CHARACTERISTICS:
( A ) LENGTH: 862 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ala His Thr Phe Arg Gly Cys Ser Leu Ala Phe Met Phe Ile Ile
  1               5                  10                 15
Thr Trp Leu Leu Ile Lys Ala Lys Ile Asp Ala Cys Lys Arg Gly Asp
             20                  25                 30
Val Thr Val Lys Pro Ser His Val Ile Leu Leu Gly Ser Thr Val Asn
             35                  40                 45
Ile Thr Cys Ser Leu Lys Pro Arg Gln Gly Cys Phe His Tyr Ser Arg
         50                  55                 60
Arg Asn Lys Leu Ile Leu Tyr Lys Phe Asp Arg Arg Ile Asn Phe His
 65                  70                 75                 80
His Gly His Ser Leu Asn Ser Gln Val Thr Gly Leu Pro Leu Gly Thr
                 85                  90                 95
Thr Leu Phe Val Cys Lys Leu Ala Cys Ile Asn Ser Asp Glu Ile Gln
                100                 105                110
Ile Cys Gly Ala Glu Ile Phe Val Gly Val Ala Pro Glu Gln Pro Gln
            115                 120                 125
Asn Leu Ser Cys Ile Gln Lys Gly Glu Gln Gly Thr Val Ala Cys Thr
130                 135                 140
Trp Glu Arg Gly Arg Asp Thr His Leu Tyr Thr Glu Tyr Thr Leu Gln
145                 150                 155                 160
Leu Ser Gly Pro Lys Asn Leu Thr Trp Gln Lys Gln Cys Lys Asp Ile
                165                 170                 175
Tyr Cys Asp Tyr Leu Asp Phe Gly Ile Asn Leu Thr Pro Glu Ser Pro
            180                 185                 190
Glu Ser Asn Phe Thr Ala Lys Val Thr Ala Val Asn Ser Leu Gly Ser
            195                 200                 205
Ser Ser Ser Leu Pro Ser Thr Phe Thr Phe Leu Asp Ile Val Arg Pro
210                 215                 220
Leu Pro Pro Trp Asp Ile Arg Ile Lys Phe Gln Lys Ala Ser Val Ser
225                 230                 235                 240
Arg Cys Thr Leu Tyr Trp Arg Asp Glu Gly Leu Val Leu Leu Asn Arg
                245                 250                 255
Leu Arg Tyr Arg Pro Ser Asn Ser Arg Leu Trp Asn Met Val Asn Val
            260                 265                 270
Thr Lys Ala Lys Gly Arg His Asp Leu Leu Asp Leu Lys Pro Phe Thr
            275                 280                 285
Glu Tyr Glu Phe Gln Ile Ser Ser Lys Leu His Leu Tyr Lys Gly Ser
            290                 295                 300
Trp Ser Asp Trp Ser Glu Ser Leu Arg Ala Gln Thr Pro Glu Glu Glu
305                 310                 315                 320
Pro Thr Gly Met Leu Asp Val Trp Tyr Met Lys Arg His Ile Asp Tyr
                325                 330                 335
Ser Arg Gln Gln Ile Ser Leu Phe Trp Lys Asn Leu Ser Val Ser Glu
            340                 345                 350
```

| | | | | | | | | | | | | | | |
|---|---|---|---|---|---|---|---|---|---|---|---|---|---|---|
| Ala | Arg | Gly | Lys | Ile | Leu | His | Tyr | Gln | Val | Thr | Leu | Gln | Glu | Leu | Thr |
| | | 355 | | | | | 360 | | | | 365 | | | | |
| Gly | Gly | Lys | Ala | Met | Thr | Gln | Asn | Ile | Thr | Gly | His | Thr | Ser | Trp | Thr |
| | 370 | | | | | 375 | | | | | 380 | | | | |
| Thr | Val | Ile | Pro | Arg | Thr | Gly | Asn | Trp | Ala | Val | Ala | Val | Ser | Ala | Ala |
| 385 | | | | | 390 | | | | | 395 | | | | | 400 |
| Asn | Ser | Lys | Gly | Ser | Ser | Leu | Pro | Thr | Arg | Ile | Asn | Ile | Met | Asn | Leu |
| | | | | 405 | | | | | 410 | | | | 415 | | |
| Cys | Glu | Ala | Gly | Leu | Leu | Ala | Pro | Arg | Gln | Val | Ser | Ala | Asn | Ser | Glu |
| | | | 420 | | | | | 425 | | | | | 430 | | |
| Gly | Met | Asp | Asn | Ile | Leu | Val | Thr | Trp | Gln | Pro | Pro | Arg | Lys | Asp | Pro |
| | | 435 | | | | | 440 | | | | | 445 | | | |
| Ser | Ala | Val | Gln | Glu | Tyr | Val | Val | Glu | Trp | Arg | Glu | Leu | His | Pro | Gly |
| | 450 | | | | | 455 | | | | | 460 | | | | |
| Gly | Asp | Thr | Gln | Val | Pro | Leu | Asn | Trp | Leu | Arg | Ser | Arg | Pro | Tyr | Asn |
| 465 | | | | | 470 | | | | | 475 | | | | | 480 |
| Val | Ser | Ala | Leu | Ile | Ser | Glu | Asn | Ile | Lys | Ser | Tyr | Ile | Cys | Tyr | Glu |
| | | | | 485 | | | | | 490 | | | | | 495 | |
| Ile | Arg | Val | Tyr | Ala | Leu | Ser | Gly | Asp | Gln | Gly | Gly | Cys | Ser | Ser | Ile |
| | | | 500 | | | | | 505 | | | | 510 | | | |
| Leu | Gly | Asn | Ser | Lys | His | Lys | Ala | Pro | Leu | Ser | Gly | Pro | His | Ile | Asn |
| | | 515 | | | | | 520 | | | | | 525 | | | |
| Ala | Ile | Thr | Glu | Glu | Lys | Gly | Ser | Ile | Leu | Ile | Ser | Trp | Asn | Ser | Ile |
| | 530 | | | | | 535 | | | | | 540 | | | | |
| Pro | Val | Gln | Glu | Gln | Met | Gly | Cys | Leu | Leu | His | Tyr | Arg | Ile | Tyr | Trp |
| 545 | | | | | 550 | | | | | 555 | | | | | 560 |
| Lys | Glu | Arg | Asp | Ser | Asn | Ser | Gln | Pro | Gln | Leu | Cys | Glu | Ile | Pro | Tyr |
| | | | | 565 | | | | | 570 | | | | | 575 | |
| Arg | Val | Ser | Gln | Asn | Ser | His | Pro | Ile | Asn | Ser | Leu | Gln | Pro | Arg | Val |
| | | | 580 | | | | | 585 | | | | | 590 | | |
| Thr | Tyr | Val | Leu | Trp | Met | Thr | Ala | Leu | Thr | Ala | Ala | Gly | Glu | Ser | Ser |
| | | 595 | | | | | 600 | | | | | 605 | | | |
| His | Gly | Asn | Glu | Arg | Glu | Phe | Cys | Leu | Gln | Gly | Lys | Ala | Asn | Trp | Met |
| 610 | | | | | 615 | | | | | 620 | | | | | |
| Ala | Phe | Val | Ala | Pro | Ser | Ile | Cys | Ile | Ala | Ile | Ile | Met | Val | Gly | Ile |
| 625 | | | | | 630 | | | | | 635 | | | | | 640 |
| Phe | Ser | Thr | His | Tyr | Phe | Gln | Gln | Lys | Val | Phe | Val | Leu | Leu | Ala | Ala |
| | | | | 645 | | | | | 650 | | | | | 655 | |
| Leu | Arg | Pro | Gln | Trp | Cys | Ser | Arg | Glu | Ile | Pro | Asp | Pro | Ala | Asn | Ser |
| | | | | 660 | | | | | 665 | | | | 670 | | |
| Thr | Cys | Ala | Lys | Lys | Tyr | Pro | Ile | Ala | Glu | Glu | Lys | Thr | Gln | Leu | Pro |
| | | | 675 | | | | | 680 | | | | 685 | | | |
| Leu | Asp | Arg | Leu | Leu | Ile | Asp | Trp | Pro | Thr | Pro | Glu | Asp | Pro | Glu | Pro |
| | 690 | | | | | 695 | | | | | 700 | | | | |
| Leu | Val | Ile | Ser | Glu | Val | Leu | His | Gln | Val | Thr | Pro | Val | Phe | Arg | His |
| 705 | | | | | | 710 | | | | | 715 | | | | 720 |
| Pro | Pro | Cys | Ser | Asn | Trp | Pro | Gln | Arg | Glu | Lys | Gly | Ile | Gln | Gly | His |
| | | | | 725 | | | | | 730 | | | | | 735 | |
| Gln | Ala | Ser | Glu | Lys | Asp | Met | Met | His | Ser | Ala | Ser | Ser | Pro | Pro | Pro |
| | | | 740 | | | | | 745 | | | | | 750 | | |
| Pro | Arg | Ala | Leu | Gln | Ala | Glu | Ser | Arg | Gln | Leu | Val | Asp | Leu | Tyr | Lys |
| | | 755 | | | | | 760 | | | | | 765 | | | |
| Val | Leu | Glu | Ser | Arg | Gly | Ser | Asp | Pro | Lys | Pro | Glu | Asn | Pro | Ala | Cys |
| 770 | | | | | 775 | | | | | 780 | | | | | |

```
Pro  Trp  Thr  Val  Leu  Pro  Ala  Gly  Asp  Leu  Pro  Thr  His  Asp  Gly  Tyr
785                      790                      795                      800

Leu  Pro  Ser  Asn  Ile  Asp  Asp  Leu  Pro  Ser  His  Glu  Ala  Pro  Leu  Ala
                    805                      810                      815

Asp  Ser  Leu  Glu  Glu  Leu  Glu  Pro  Gln  His  Ile  Ser  Leu  Ser  Val  Phe
               820                      825                      830

Pro  Ser  Ser  Ser  Leu  His  Pro  Leu  Thr  Phe  Ser  Cys  Gly  Asp  Lys  Leu
          835                      840                      845

Thr  Leu  Asp  Gln  Leu  Lys  Met  Arg  Cys  Asp  Ser  Leu  Met  Leu
     850                 855                      860
```

( 2 ) INFORMATION FOR SEQ ID NO:3:

( i ) SEQUENCE CHARACTERISTICS:
        ( A ) LENGTH: 2104 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( v i ) ORIGINAL SOURCE:
        ( A ) ORGANISM: Homo sapiens
        ( G ) CELL TYPE: human T-cells ( v i i ) IMMEDIATE SOURCE:
        ( A ) LIBRARY: library 3 day PHA/pEF- BOS
        ( B ) CLONE: human interleukin-12 receptor clone #5

( i x ) FEATURE:
        ( A ) NAME/KEY: CDS
        ( B ) LOCATION: 65..2050

( x i ) SEQUENCE DESCRIPTION: SEQ ID NO:3:

```
GGTGGCTGAA  CCTCGCAGGT  GGCAGAGAGG  CTCCCCTGGG  GCTGTGGGGC  TCTACGTGGA         60

TCCG ATG GAG CCG CTG GTG ACC TGG GTG GTC CCC CTC CTC TTC CTC TTC              109
     Met Glu Pro Leu Val Thr Trp Val Val Pro Leu Leu Phe Leu Phe
     1               5                   10                  15

CTG CTG TCC AGG CAG GGC GCT GCC TGC AGA ACC AGT GAG TGC TGT TTT              157
Leu Leu Ser Arg Gln Gly Ala Ala Cys Arg Thr Ser Glu Cys Cys Phe
                20                  25                  30

CAG GAC CCG CCA TAT CCG GAT GCA GAC TCA GGC TCG GCC TCG GGC CCT              205
Gln Asp Pro Pro Tyr Pro Asp Ala Asp Ser Gly Ser Ala Ser Gly Pro
            35                  40                  45

AGG GAC CTG AGA TGC TAT CGG ATA TCC AGT GAT CGT TAC GAG TGC TCC              253
Arg Asp Leu Arg Cys Tyr Arg Ile Ser Ser Asp Arg Tyr Glu Cys Ser
        50                  55                  60

TGG CAG TAT GAG GGT CCC ACA GCT GGG GTC AGC CAC TTC CTG CGG TGT              301
Trp Gln Tyr Glu Gly Pro Thr Ala Gly Val Ser His Phe Leu Arg Cys
    65                  70                  75

TGC CTT AGC TCC GGG CGC TGC TGC TAC TTC GCC GCC GGC TCA GCC ACC              349
Cys Leu Ser Ser Gly Arg Cys Cys Tyr Phe Ala Ala Gly Ser Ala Thr
80                  85                  90                  95

AGG CTG CAG TTC TCC GAC CAG GCT GGG GTG TCT GTG CTG TAC ACT GTC              397
Arg Leu Gln Phe Ser Asp Gln Ala Gly Val Ser Val Leu Tyr Thr Val
            100                 105                 110

ACA CTC TGG GTG GAA TCC TGG GCC AGG AAC CAG ACA GAG AAG TCT CCT              445
Thr Leu Trp Val Glu Ser Trp Ala Arg Asn Gln Thr Glu Lys Ser Pro
        115                 120                 125

GAG GTG ACC CTG CAG CTC TAC AAC TCA GTT AAA TAT GAG CCT CCT CTG              493
Glu Val Thr Leu Gln Leu Tyr Asn Ser Val Lys Tyr Glu Pro Pro Leu
    130                 135                 140
```

| | | | | | | | | | | | | | | | | |
|---|---|---|---|---|---|---|---|---|---|---|---|---|---|---|---|---|
| GGA | GAC | ATC | AAG | GTG | TCC | AAG | TTG | GCC | GGG | CAG | CTG | CGT | ATG | GAG | TGG | 541 |
| Gly | Asp | Ile | Lys | Val | Ser | Lys | Leu | Ala | Gly | Gln | Leu | Arg | Met | Glu | Trp | |
| | | | 145 | | | 150 | | | | | | | 155 | | | |
| GAG | ACC | CCG | GAT | AAC | CAG | GTT | GGT | GCT | GAG | GTG | CAG | TTC | CGG | CAC | CGG | 589 |
| Glu | Thr | Pro | Asp | Asn | Gln | Val | Gly | Ala | Glu | Val | Gln | Phe | Arg | His | Arg | |
| 160 | | | | | 165 | | | | | 170 | | | | | 175 | |
| ACA | CCC | AGC | AGC | CCA | TGG | AAG | TTG | GGC | GAC | TGC | GGA | CCT | CAG | GAT | GAT | 637 |
| Thr | Pro | Ser | Ser | Pro | Trp | Lys | Leu | Gly | Asp | Cys | Gly | Pro | Gln | Asp | Asp | |
| | | | | 180 | | | | | 185 | | | | | 190 | | |
| GAT | ACT | GAG | TCC | TGC | CTC | TGC | CCC | CTG | GAG | ATG | AAT | GTG | GCC | CAG | GAA | 685 |
| Asp | Thr | Glu | Ser | Cys | Leu | Cys | Pro | Leu | Glu | Met | Asn | Val | Ala | Gln | Glu | |
| | | | 195 | | | | | 200 | | | | | 205 | | | |
| TTC | CAG | CTC | CGA | CGA | CGG | CAG | CTG | GGG | AGC | CAA | GGA | AGT | TCC | TGG | AGC | 733 |
| Phe | Gln | Leu | Arg | Arg | Arg | Gln | Leu | Gly | Ser | Gln | Gly | Ser | Ser | Trp | Ser | |
| | | 210 | | | | | 215 | | | | | 220 | | | | |
| AAG | TGG | AGC | AGC | CCC | GTG | TGC | GTT | CCC | CCT | GAA | AAC | CCC | CCA | CAG | CCT | 781 |
| Lys | Trp | Ser | Ser | Pro | Val | Cys | Val | Pro | Pro | Glu | Asn | Pro | Pro | Gln | Pro | |
| s | | | 225 | | | | | 230 | | | | | 235 | | | |
| CAG | GTG | AGA | TTC | TCG | GTG | GAG | CAG | CTG | GGC | CAG | GAT | GGG | AGG | AGG | CGG | 829 |
| Gln | Val | Arg | Phe | Ser | Val | Glu | Gln | Leu | Gly | Gln | Asp | Gly | Arg | Arg | Arg | |
| 240 | | | | | 245 | | | | | 250 | | | | | 255 | |
| CTG | ACC | CTG | AAA | GAG | CAG | CCA | ACC | CAG | CTG | GAG | CTT | CCA | GAA | GGC | TGT | 877 |
| Leu | Thr | Leu | Lys | Glu | Gln | Pro | Thr | Gln | Leu | Glu | Leu | Pro | Glu | Gly | Cys | |
| | | | | 260 | | | | | 265 | | | | | 270 | | |
| CAA | GGG | CTG | GCG | CCT | GGC | ACG | GAG | GTC | ACT | TAC | CGA | CTA | CAG | CTC | CAC | 925 |
| Gln | Gly | Leu | Ala | Pro | Gly | Thr | Glu | Val | Thr | Tyr | Arg | Leu | Gln | Leu | His | |
| | | | 275 | | | | | 280 | | | | | 285 | | | |
| ATG | CTG | TCC | TGC | CCG | TGT | AAG | GCC | AAG | GCC | ACC | AGG | ACC | CTG | CAC | CTG | 973 |
| Met | Leu | Ser | Cys | Pro | Cys | Lys | Ala | Lys | Ala | Thr | Arg | Thr | Leu | His | Leu | |
| | | 290 | | | | | 295 | | | | | 300 | | | | |
| GGG | AAG | ATG | CCC | TAT | CTC | TCG | GGT | GCT | GCC | TAC | AAC | GTG | GCT | GTC | ATC | 1021 |
| Gly | Lys | Met | Pro | Tyr | Leu | Ser | Gly | Ala | Ala | Tyr | Asn | Val | Ala | Val | Ile | |
| 305 | | | | | 310 | | | | | 315 | | | | | | |
| TCC | TCG | AAC | CAA | TTT | GGT | CCT | GGC | CTG | AAC | CAG | ACG | TGG | CAC | ATT | CCT | 1069 |
| Ser | Ser | Asn | Gln | Phe | Gly | Pro | Gly | Leu | Asn | Gln | Thr | Trp | His | Ile | Pro | |
| 320 | | | | | 325 | | | | | 330 | | | | | 335 | |
| GCC | GAC | ACC | CAC | ACA | GAA | CCA | GTG | GCT | CTG | AAT | ATC | AGC | GTC | GGA | ACC | 1117 |
| Ala | Asp | Thr | His | Thr | Glu | Pro | Val | Ala | Leu | Asn | Ile | Ser | Val | Gly | Thr | |
| | | | | 340 | | | | | 345 | | | | | 350 | | |
| AAC | GGG | ACC | ACC | ATG | TAT | TGG | CCA | GCC | CGG | GCT | CAG | AGC | ATG | ACG | TAT | 1165 |
| Asn | Gly | Thr | Thr | Met | Tyr | Trp | Pro | Ala | Arg | Ala | Gln | Ser | Met | Thr | Tyr | |
| | | | 355 | | | | | 360 | | | | | 365 | | | |
| TGC | ATT | GAA | TGG | CAG | CCT | GTG | GGC | CAG | GAC | GGG | GGC | CTT | GCC | ACC | TGC | 1213 |
| Cys | Ile | Glu | Trp | Gln | Pro | Val | Gly | Gln | Asp | Gly | Gly | Leu | Ala | Thr | Cys | |
| | | 370 | | | | | 375 | | | | | 380 | | | | |
| AGC | CTG | ACT | GCG | CCG | CAA | GAC | CCG | GAT | CCG | GCT | GGA | ATG | GCA | ACC | TAC | 1261 |
| Ser | Leu | Thr | Ala | Pro | Gln | Asp | Pro | Asp | Pro | Ala | Gly | Met | Ala | Thr | Tyr | |
| | | 385 | | | | | 390 | | | | | 395 | | | | |
| AGC | TGG | AGT | CGA | GAG | TCT | GGG | GCA | ATG | GGG | CAG | GAA | AAG | TGT | TAC | TAC | 1309 |
| Ser | Trp | Ser | Arg | Glu | Ser | Gly | Ala | Met | Gly | Gln | Glu | Lys | Cys | Tyr | Tyr | |
| 400 | | | | | 405 | | | | | 410 | | | | | 415 | |
| ATT | ACC | ATC | TTT | GCC | TCT | GCG | CAC | CCC | GAG | AAG | CTC | ACC | TTG | TGG | TCT | 1357 |
| Ile | Thr | Ile | Phe | Ala | Ser | Ala | His | Pro | Glu | Lys | Leu | Thr | Leu | Trp | Ser | |
| | | | | 420 | | | | | 425 | | | | | 430 | | |
| ACG | GTC | CTG | TCC | ACC | TAC | CAC | TTT | GGG | GGC | AAT | GCC | TCA | GCA | GCT | GGG | 1405 |
| Thr | Val | Leu | Ser | Thr | Tyr | His | Phe | Gly | Gly | Asn | Ala | Ser | Ala | Ala | Gly | |
| | | | 435 | | | | | 440 | | | | | 445 | | | |
| ACA | CCG | CAC | CAC | GTC | TCG | GTG | AAG | AAT | CAT | AGC | TTG | GAC | TCT | GTG | TCT | 1453 |
| Thr | Pro | His | His | Val | Ser | Val | Lys | Asn | His | Ser | Leu | Asp | Ser | Val | Ser | |
| | | 450 | | | | | 455 | | | | | 460 | | | | |

```
GTG  GAC  TGG  GCA  CCA  TCC  CTG  CTG  AGC  ACC  TGT  CCC  GGC  GTC  CTA  AAG    1501
Val  Asp  Trp  Ala  Pro  Ser  Leu  Leu  Ser  Thr  Cys  Pro  Gly  Val  Leu  Lys
465                           470                      475

GAG  TAT  GTT  GTC  CGC  TGC  CGA  GAT  GAA  GAC  AGC  AAA  CAG  GTG  TCA  GAG    1549
Glu  Tyr  Val  Val  Arg  Cys  Arg  Asp  Glu  Asp  Ser  Lys  Gln  Val  Ser  Glu
480                      485                      490                           495

CAT  CCC  GTG  CAG  CCC  ACA  GAG  ACC  CAA  GTT  ACC  CTC  AGT  GGC  CTG  CGG    1597
His  Pro  Val  Gln  Pro  Thr  Glu  Thr  Gln  Val  Thr  Leu  Ser  Gly  Leu  Arg
                    500                      505                      510

GCT  GGT  GTA  GCC  TAC  ACG  GTG  CAG  GTG  CGA  GCA  GAC  ACA  GCG  TGG  CTG    1645
Ala  Gly  Val  Ala  Tyr  Thr  Val  Gln  Val  Arg  Ala  Asp  Thr  Ala  Trp  Leu
               515                      520                      525

AGG  GGT  GTC  TGG  AGC  CAG  CCC  CAG  CGC  TTC  AGC  ATC  GAA  GTG  CAG  GTT    1693
Arg  Gly  Val  Trp  Ser  Gln  Pro  Gln  Arg  Phe  Ser  Ile  Glu  Val  Gln  Val
          530                      535                      540

TCT  GAT  TGG  CTC  ATC  TTC  TTC  GCC  TCC  CTG  GGG  AGC  TTC  CTG  AGC  ATC    1741
Ser  Asp  Trp  Leu  Ile  Phe  Phe  Ala  Ser  Leu  Gly  Ser  Phe  Leu  Ser  Ile
545                           550                      555

CTT  CTC  GTG  GGC  GTC  CTT  GGC  TAC  CTT  GGC  CTG  AAC  AGG  GCC  GCA  CGG    1789
Leu  Leu  Val  Gly  Val  Leu  Gly  Tyr  Leu  Gly  Leu  Asn  Arg  Ala  Ala  Arg
560                      565                      570                      575

CAC  CTG  TGC  CCG  CCG  CTG  CCC  ACA  CCC  TGT  GCC  AGC  TCC  GCC  ATT  GAG    1837
His  Leu  Cys  Pro  Pro  Leu  Pro  Thr  Pro  Cys  Ala  Ser  Ser  Ala  Ile  Glu
                    580                      585                      590

TTC  CCT  GGA  GGG  AAG  GAG  ACT  TGG  CAG  TGG  ATC  AAC  CCA  GTG  GAC  TTC    1885
Phe  Pro  Gly  Gly  Lys  Glu  Thr  Trp  Gln  Trp  Ile  Asn  Pro  Val  Asp  Phe
               595                      600                      605

CAG  GAA  GAG  GCA  TCC  CTG  CAG  GAG  GCC  CTG  GTG  GTA  GAG  ATG  TCC  TGG    1933
Gln  Glu  Glu  Ala  Ser  Leu  Gln  Glu  Ala  Leu  Val  Val  Glu  Met  Ser  Trp
          610                      615                      620

GAC  AAA  GGC  GAG  AGG  ACT  GAG  CCT  CTC  GAG  AAG  ACA  GAG  CTA  CCT  GAG    1981
Asp  Lys  Gly  Glu  Arg  Thr  Glu  Pro  Leu  Glu  Lys  Thr  Glu  Leu  Pro  Glu
625                           630                      635

GGT  GCC  CCT  GAG  CTG  GCC  CTG  GAT  ACA  GAG  TTG  TCC  TTG  GAG  GAT  GGA    2029
Gly  Ala  Pro  Glu  Leu  Ala  Leu  Asp  Thr  Glu  Leu  Ser  Leu  Glu  Asp  Gly
640                      645                      650                      655

GAC  AGG  TGC  AAG  GCC  AAG  ATG  TGATCGTTGA  GGCTCAGAGA  GGGTGAGTGA             2080
Asp  Arg  Cys  Lys  Ala  Lys  Met
                    660

CTCGCCCGAG  GCTACGTAGC  CTTT                                                     2104
```

( 2 ) INFORMATION FOR SEQ ID NO:4:

( i ) SEQUENCE CHARACTERISTICS:
        ( A ) LENGTH: 662 amino acids
        ( B ) TYPE: amino acid
        ( D ) TOPOLOGY: linear ( i i ) MOLECULE TYPE: protein ( i x ) FEATURE:
        ( A ) NAME/KEY: Region
        ( B ) LOCATION: 1..20
        ( D ) OTHER INFORMATION: /note= "N-terminal signal peptide
            ( 1 . . 2 0   o r   2 3   o r   2 4 )"

( i x ) FEATURE:
        ( A ) NAME/KEY: Region
        ( B ) LOCATION: 541..570
        ( D ) OTHER INFORMATION: /note= "transmembrane region"

( i x ) FEATURE:
        ( A ) NAME/KEY: Region
        ( B ) LOCATION: 571..662
        ( D ) OTHER INFORMATION: /note= "cytoplasmic tail region"

( i x ) FEATURE:
    ( A ) NAME/KEY: Region
    ( B ) LOCATION: 52..64
    ( D ) OTHER INFORMATION: /note= "sequence motif of cytokine
        receptor superfamily Cys52..Cys62SW"

( i x ) FEATURE:
    ( A ) NAME/KEY: Region
    ( B ) LOCATION: 222..226
    ( D ) OTHER INFORMATION: /note= "cytokine receptor
        superfamily motif (W222SKWS)"

( i x ) FEATURE:
    ( A ) NAME/KEY: Region
    ( B ) LOCATION: 121..123
    ( D ) OTHER INFORMATION: /note= "N-linked glycosylation
        site"

( i x ) FEATURE:
    ( A ) NAME/KEY: Region
    ( B ) LOCATION: 329..331
    ( D ) OTHER INFORMATION: /note= "N-linked glycosylation
        site"

( i x ) FEATURE:
    ( A ) NAME/KEY: Region
    ( B ) LOCATION: 346..348
    ( D ) OTHER INFORMATION: /note= "N-linked glycosylation
        site"

( i x ) FEATURE:
    ( A ) NAME/KEY: Region
    ( B ) LOCATION: 352..354
    ( D ) OTHER INFORMATION: /note= "N-linked glycosylation
        site"

( i x ) FEATURE:
    ( A ) NAME/KEY: Region
    ( B ) LOCATION: 442..444
    ( D ) OTHER INFORMATION: /note= "N-linked glycosylation
        site"

( i x ) FEATURE:
    ( A ) NAME/KEY: Region
    ( B ) LOCATION: 456..458
    ( D ) OTHER INFORMATION: /note= "N-linked glycosylation
        site"

( i x ) FEATURE:
    ( A ) NAME/KEY: Region
    ( B ) LOCATION: 24..540
    ( D ) OTHER INFORMATION: /note= "Extracellular region"

( x i ) SEQUENCE DESCRIPTION: SEQ ID NO:4:

```
Met Glu Pro Leu Val Thr Trp Val Val Pro Leu Leu Phe Leu Phe Leu
 1               5                  10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
                100                 105                 110

Leu Trp Val Glu Ser Trp Ala Arg Asn Gln Thr Glu Lys Ser Pro Glu
            115                 120                 125
```

-continued

```
Val  Thr  Leu  Gln  Leu  Tyr  Asn  Ser  Val  Lys  Tyr  Glu  Pro  Pro  Leu  Gly
     130                      135                 140

Asp  Ile  Lys  Val  Ser  Lys  Leu  Ala  Gly  Gln  Leu  Arg  Met  Glu  Trp  Glu
145                      150                      155                      160

Thr  Pro  Asp  Asn  Gln  Val  Gly  Ala  Glu  Val  Gln  Phe  Arg  His  Arg  Thr
               165                      170                           175

Pro  Ser  Ser  Pro  Trp  Lys  Leu  Gly  Asp  Cys  Gly  Pro  Gln  Asp  Asp
               180                      185                      190

Thr  Glu  Ser  Cys  Leu  Cys  Pro  Leu  Glu  Met  Asn  Val  Ala  Gln  Glu  Phe
          195                      200                      205

Gln  Leu  Arg  Arg  Arg  Gln  Leu  Gly  Ser  Gln  Gly  Ser  Ser  Trp  Ser  Lys
     210                      215                 220

Trp  Ser  Ser  Pro  Val  Cys  Val  Pro  Pro  Glu  Asn  Pro  Pro  Gln  Pro  Gln
225                      230                      235                      240

Val  Arg  Phe  Ser  Val  Glu  Gln  Leu  Gly  Gln  Asp  Gly  Arg  Arg  Arg  Leu
               245                      250                           255

Thr  Leu  Lys  Glu  Gln  Pro  Thr  Gln  Leu  Glu  Leu  Pro  Glu  Gly  Cys  Gln
          260                      265                 270

Gly  Leu  Ala  Pro  Gly  Thr  Glu  Val  Thr  Tyr  Arg  Leu  Gln  Leu  His  Met
               275                      280                 285

Leu  Ser  Cys  Pro  Cys  Lys  Ala  Lys  Ala  Thr  Arg  Thr  Leu  His  Leu  Gly
     290                      295                 300

Lys  Met  Pro  Tyr  Leu  Ser  Gly  Ala  Ala  Tyr  Asn  Val  Ala  Val  Ile  Ser
305                      310                      315                      320

Ser  Asn  Gln  Phe  Gly  Pro  Gly  Leu  Asn  Gln  Thr  Trp  His  Ile  Pro  Ala
               325                      330                           335

Asp  Thr  His  Thr  Glu  Pro  Val  Ala  Leu  Asn  Ile  Ser  Val  Gly  Thr  Asn
               340                      345                 350

Gly  Thr  Thr  Met  Tyr  Trp  Pro  Ala  Arg  Ala  Gln  Ser  Met  Thr  Tyr  Cys
          355                      360                 365

Ile  Glu  Trp  Gln  Pro  Val  Gly  Gln  Asp  Gly  Gly  Leu  Ala  Thr  Cys  Ser
     370                      375                 380

Leu  Thr  Ala  Pro  Gln  Asp  Pro  Asp  Pro  Ala  Gly  Met  Ala  Thr  Tyr  Ser
385                      390                      395                      400

Trp  Ser  Arg  Glu  Ser  Gly  Ala  Met  Gly  Gln  Glu  Lys  Cys  Tyr  Tyr  Ile
               405                      410                           415

Thr  Ile  Phe  Ala  Ser  Ala  His  Pro  Glu  Lys  Leu  Thr  Leu  Trp  Ser  Thr
               420                      425                 430

Val  Leu  Ser  Thr  Tyr  His  Phe  Gly  Gly  Asn  Ala  Ser  Ala  Ala  Gly  Thr
          435                      440                 445

Pro  His  His  Val  Ser  Val  Lys  Asn  His  Ser  Leu  Asp  Ser  Val  Ser  Val
     450                      455                 460

Asp  Trp  Ala  Pro  Ser  Leu  Leu  Ser  Thr  Cys  Pro  Gly  Val  Leu  Lys  Glu
465                      470                      475                      480

Tyr  Val  Val  Arg  Cys  Arg  Asp  Glu  Asp  Ser  Lys  Gln  Val  Ser  Glu  His
               485                      490                           495

Pro  Val  Gln  Pro  Thr  Glu  Thr  Gln  Val  Thr  Leu  Ser  Gly  Leu  Arg  Ala
               500                      505                 510

Gly  Val  Ala  Tyr  Thr  Val  Gln  Val  Arg  Ala  Asp  Thr  Ala  Trp  Leu  Arg
          515                      520                 525

Gly  Val  Trp  Ser  Gln  Pro  Gln  Arg  Phe  Ser  Ile  Glu  Val  Gln  Val  Ser
          530                      535                 540

Asp  Trp  Leu  Ile  Phe  Phe  Ala  Ser  Leu  Gly  Ser  Phe  Leu  Ser  Ile  Leu
545                      550                      555                      560
```

```
Leu  Val  Gly  Val  Leu  Gly  Tyr  Leu  Gly  Leu  Asn  Arg  Ala  Ala  Arg  His
               565                      570                          575

Leu  Cys  Pro  Pro  Leu  Pro  Thr  Pro  Cys  Ala  Ser  Ser  Ala  Ile  Glu  Phe
               580                      585                     590

Pro  Gly  Gly  Lys  Glu  Thr  Trp  Gln  Trp  Ile  Asn  Pro  Val  Asp  Phe  Gln
          595                      600                     605

Glu  Glu  Ala  Ser  Leu  Gln  Glu  Ala  Leu  Val  Val  Glu  Met  Ser  Trp  Asp
     610                      615                     620

Lys  Gly  Glu  Arg  Thr  Glu  Pro  Leu  Glu  Lys  Thr  Glu  Leu  Pro  Glu  Gly
625                      630                     635                          640

Ala  Pro  Glu  Leu  Ala  Leu  Asp  Thr  Glu  Leu  Ser  Leu  Glu  Asp  Gly  Asp
               645                      650                          655

Arg  Cys  Lys  Ala  Lys  Met
               660
```